US012758689B2

(12) United States Patent
Alvarez-Puebla et al.

(10) Patent No.: US 12,758,689 B2
(45) Date of Patent: Oct. 13, 2026

(54) DEVICE AND METHOD FOR THE PREPARATION OF PLATELET RICH PLASMA

(71) Applicants: UNIVERSITAT ROVIRA i VIRGILI, Tarragona (ES); INSTITUCIÓ CATALANA DE RECERCA I ESTUDIS AVANÇATS, Barcelona (ES); FUNDACIÓ PRIVADA CENTRE TECNOLÒGIC DE LA

(Continued)

(72) Inventors: Ramon Angel Alvarez-Puebla, Tarragona (ES); Sara Gomez de Pedro, Tarragona (ES); Manuel Garcia Algar, El Morell-Tarragona (ES); Moritz

(Continued)

(73) Assignees: UNIVERSITAT ROVIRA i VIRGILI, Tarragona (ES); INSTITUCIÓ CATALANA DE RECERCA I ESTUDIS AVANÇATS, Barcelona (ES); FUNDACIÓ EURECAT, Cerdanyola del Valles Cataluna (ES); UNIVERSITAT AUTÒNOMA DE BARCELONA, Barcelona (ES); UNIDAD DE CIRUGÍA ARTROSCÓPICA, S.L., Vitoria—Gasteiz—Alava (ES); UNIDAD DE TERAPIA BIOLÓGICA AVANZADA, S.L., Vitoria—Gasteiz—Alava (ES); MEDCOM TECH, S.A., Madrid (ES); MEDCOM ADVANCE, S.A., Barcelona (ES)

( * ) Notice: Subject to any disclaimer, the term of this patent is extended or adjusted under 35 U.S.C. 154(b) by 1263 days.

(21) Appl. No.: 16/613,068

(22) PCT Filed: May 11, 2018

(86) PCT No.: PCT/EP2018/062194
§ 371 (c)(1),
(2) Date: Nov. 12, 2019

(87) PCT Pub. No.: WO2018/206756
PCT Pub. Date: Nov. 15, 2018

(65) Prior Publication Data

US 2020/0061260 A1 Feb. 27, 2020

(30) Foreign Application Priority Data

May 12, 2017 (EP) .................................... 17382271

(51) Int. Cl.
*A61M 1/02* (2006.01)
*A61M 1/34* (2006.01)
(Continued)

(52) U.S. Cl.
CPC ........ *A61M 1/0281* (2013.01); *A61M 1/3479* (2014.02); *B01D 3/145* (2013.01);
(Continued)

(58) Field of Classification Search
CPC .............. A61M 1/0281; A61M 1/3479; A61M 2202/0427; A61M 2205/0244;
(Continued)

(56) References Cited

U.S. PATENT DOCUMENTS 4,832,839 A 5/1989 Tamura
5,871,649 A * 2/1999 Ofsthun .............. A61M 1/3486 210/651

(Continued)

FOREIGN PATENT DOCUMENTS

WO 2011044117 A3 4/2011

OTHER PUBLICATIONS

Andia, I., et al., "Basic Science: Molecular and Biological Aspects of Platelet-Rich Plasma Therapies", "Operative Techniques in Orthopaedics", 2012, pp. 3-9, vol. 22, No. 1, Publisher: Elsevier.

(Continued)

*Primary Examiner* — Pranav N Patel
(74) *Attorney, Agent, or Firm* — HULTQUIST, PLLC; Steven J. Hultquist

(57) ABSTRACT

The present invention relates to a device and method for the preparation of platelet rich plasma, and to the plasma obtained by employing said device and method. The method comprises evaporating and dialysing plasma with the device of the invention to provide a plasma enriched in platelets and non-platelet biomolecules. The plasma thus obtained shows improved regenerative properties with respect to other plasma preparations.

12 Claims, 10 Drawing Sheets
(10 of 10 Drawing Sheet(s) Filed in Color)

(71) Applicants: QUÍMICA DE CATALUNYA, Tarragona (ES); UNIVERSITAT AUTÒNOMA DE BARCELONA, Barcelona (ES); UNIDAD DE CIRUGÍA ARTROSCÓPICA, S.L., Vitoria-Gasteiz-Alava (ES); UNIDAD DE TERAPIA BIOLÓGICA AVANZADA, S.L., Vitoria-Gasteiz-Alava (ES); MEDCOM TECH, S.A., Madrid (ES); MEDCOM ADVANCE, S.A., Barcelona (ES)

(72) Inventors: Julian Nazarenus, Tarragona (ES); Xiaotong Feng, Tarragona (ES); Mikel Sanchez Alvarez, Vitoria-Gasteiz-Alava (ES); Pello Sanchez Arizmendiarrieta, Vitoria-Gasteiz-Alava (ES); Diego Delgado San Vicente, Vitoria-Gasteiz-Alava (ES); Ane Garate Letona, Vitoria-Gasteiz-Alava (ES); Julian Alonso Chamarro, Barcelona (ES); Maria del Mar Puyol Bosch, Castelldefels-Barcelona (ES); Antonio Calvo Lopez, Llinars del Valles-Barcelona (ES)

(51) Int. Cl.
*B01D 3/14* (2006.01)
*B01D 19/00* (2006.01)

(52) U.S. Cl.
CPC . *B01D 19/0031* (2013.01); *A61M 2202/0427* (2013.01); *A61M 2205/0244* (2013.01)

(58) Field of Classification Search
CPC ................ B01D 3/145; B01D 19/0031; B01D 63/08–088; B01L 3/502753
See application file for complete search history.

(56) References Cited

U.S. PATENT DOCUMENTS

| | | | | |
|---|---|---|---|---|
| 2004/0084370 | A1* | 5/2004 | Singh ...................... | B01F 33/30 210/500.21 |
| 2009/0060890 | A1* | 3/2009 | Humes .................... | A61P 37/02 435/308.1 |
| 2012/0184940 | A1 | 7/2012 | Ying et al. | |
| 2017/0096629 | A1 | 4/2017 | Paullier et al. | |

OTHER PUBLICATIONS

Andia, I., et al., “Platelet-rich plasma in the conservative treatment of painful tendinopathy: a systematic review and meta-analysis of controlled studies”, “British Medial Bulletin”, 2014, pp. 99-115, vol. 110, Publisher: Oxford University Press.
Anitua, E., et a., “The effect of different drugs on the preparation and biological outcomes of plasma rich in growth factors”, “Annals of Anatomy”, 2014, pp. 423-429, vol. 196, No. 6, Publisher: Elsevier.
Arnoczky, S., et al., “The Basic Science of Platelet-rich Plasma (PRP): What Clinicians Need to Know”, “Sports Med Arthrosc Rev”, Dec. 2013, pp. 180-185, vol. 21, No. 4, Publisher: www.sportsmedarthro.com.
Barclay, L., et al., “Platelet-Rich Plasma Procedure May Improve Facial Appearance”, “Medscape Plastic Surgery”, Mar. 6, 2012.
Brick, N., “Autologous Platelet-Rich Plasma for Treating Chronic Wounds”, “Am J Nurs”, Aug. 2013, p. 54, vol. 113, No. 8, Publisher: Cochrane Library.
De Jong, J., et al., “Membranes and microfluidics: a review”, “Lab Chip”, 2006, pp. 1125-1139, vol. 6, Publisher: The Royal Society of Chemistry.
Delong, J., et al., “Platelet-Rich Plasma: The PAW Classification System”, “Arthroscopy: The Journal of Arthroscopic and Related Surgery”, Jul. 2012, pp. 998-1009, vol. 28, No. 7.
Dhillon, R., et al., “Arthritis Research and Therapy”, 2012, p. 219, vol. 14, Publisher: http://arthritis-research.com/content/14/4/219.
Erickson, D., et al., “Smartphone technology can be transformative to the deployment of lab-on-chip diagnostics”, “Department of Health and Human Services”, Sep. 7, 2014, pp. 3159-3164, vol. 17, Publisher: HHS Public Access.
Filardo, G., et al., “Platelet-Rich Plasma for Knee Osteoarthritis”, “The American Journal of Sports Medicine”, , pp. NP42-NP43, vol. 41, No. 9, Publisher: ajs.sagepub.com.
Ho, N., et al., “Sample Concentration and Purification for Point-of-Care Diagnostics”, “Conf Proc IEEE Eng Med biol Soc.”, 2012, pp. 2396-2399.
Ho, N., et al., “Sample Concentration and Purification for Point-of-Care Diagnostics”, “National Institute of Health”, 2012, pp. 2396-2399, vol. 2012, Publisher: NIH Public Access.
Hsu, W., et al., “Platelet-rich Plasma in Orthopaedic Applications: Evidence-based Recommendatons for Treatment”, “J Am Acad Orthop Surg”, Dec. 2013, pp. 739-748, vol. 21, No. 12, Publisher: American Academy of Orthopaedic Surgeons.
Imura, Y., et al., “Microcirculation System with a Dialysis Part for Bioassays Evaluating Anticancer Activity and Retention”, “Analytical Chemistry”, 2012, pp. 1683-1688, vol. 85, Publisher: ACS Publications.
Kuffler, D., “Platelet-Rich Plasma and the Elimination of Neuropathic Pain”, “Mol Neurobiol”, 2013, Page(s) DOI 10.1007/s12035-013-8494-7, Publisher: Springer Science+Business Media New York 2013.
Kushida, S., et al., “Platelet and growth factor concentrations in activated platelet-rich plasma: a comparison of seven commercial separation systems”, “J Artif Organs”, , pp. 186-192, vol. 17, No. 2, Publisher: Springer.
Mao, X., et al., “Microfluidic diagnostics for the developing world”, “Department of Health and Human Services”, 2012, pp. 1412-1416, vol. 12, No. 8, Publisher: HHS Public Access.
Marx, R., “Platelet-Rich Plasma (PRP): What is PRP and What is Not PRP”, “Implant Dentistry”, 2001, pp. 225-228, vol. 10, No. 4, Publisher: Lippincott Williams & Wilkins.
Mautner, K, et al., “A Call for a Standard Classification System for Future Biologic Research: The Rationale for New PRP Nomenclature”, “PM&R”, 2015, pp. S53-S59, vol. PM R 7 (2015), Publisher: www.pmrjournal.org.
Mei-Dan, O., et al., “The Physician and SportsMedicine”, Dec. 2010, pp. 127-135, vol. 4, No. 38, Publisher: RightsLink.
Miralles, V., et al., “A Review of Heating and Temperature Control in Microfluidic Systems: Techniques and Applications”, “Diagnostics”, 2013, pp. 33-67, vol. 3, Publisher: www.mdpi.com/journal/diagnostics/.
Montero, E., et al., “Platelet-Rich Plasma: Applications in Dermatology”, “ACTAS Dermo-Sifiliograficas”, 2014, Page(s) http://dx.doi.org/10.1016/j.ad.2013.12.021, Publisher: Elsevier Doyma.
Pallua, N., et al., “Platelet-rich plasma in burns”, “Burns”, 2010, pp. 4-8, vol. 36, Publisher: Elsevier.
“Platelet Rich Plasma: Market Snapshot”, 2016, Page(s) http://www.docstoc.com/docs/47503668.
Sackmann, E., et al., “The present and future role of mocrofluids in biomedical research”, “Nature”, Mar. 13, 2014, pp. 181-189, vol. 507, Publisher: Macmillan Publishers Limited.
Sanchez, M., et al., “Ultrasound-guided platelet-rich plasma injections for the treatment of common peroneal nerve palsy associated with multiple ligament injuries of the knee”, “Knee Surg Sports Traumatol Arthrosc”, Mar. 22, 2013, Page(s) DOI 10.1007/s00167-013-2479-y, Publisher: Springer.
Sheng, Y., et al., “Size selective DNA transport through a nanoporous membrane in a PDMS microfluidic device”, “National Institute of Health”, Mar. 7, 2012, pp. 1144-1151, vol. 137, No. 5, Publisher: NIH Public Access.

(56) References Cited

OTHER PUBLICATIONS

Sheng, Y., et al., "Isolating single stranded DNA using a microfluidic dialysis device", "National Institute of Health", Jan. 7, 2014, pp. 215-224, vol. 139, No. 1, Publisher: NIH Public Access.
Song, P., et al., "Moving towards individualized medicine with microfluidics technology", "RSC Adv.", 2014, pp. 11499-11511, vol. 4, Publisher: Royal Society of Chemistry.
Streets, A., et al., "Chip in a lab: Microfludics for next generation life science research", "Biomicrofluidics", 2013, pp. 011302 1-22, vol. 7, No. 1, Publisher: CrossMark.
Temiz, Y., et al., "Lab-on-a-chip devices: How to close and plug the lab?", "Microelectronic Engineering", 2015, pp. 156-175, vol. 132, Publisher: Elsevier.
Volpatti, L., et al., "Commercialization of microfluidic devices", "Trends in Biotechnology", Jul. 2014, pp. 347-350, vol. 32, No. 7, Publisher: Science and Society.
Willms, E., et al., "Cells release subpopulations of exosomes with distinct molecular and biological properties", "Scientific Reports", 2016, pp. 1-12, vol. 6, No. 22519, Publisher: www.nature.com/scientificreports.
Yoon, S-H, "Membrane Bioreactor Processes—Principles and Applications", 2016, Publisher: CRC Press.
Zhang, J., et al., "Rapid point-of-care concentration of bacteria in a disposable microfluidic device using maniscus dragging effect", "Department of Health and Human Services", Dec. 7, 2010, pp. 3265-3270, vol. 10, No. 23, Publisher: HHS Public Access.
Zhang, H., et al., "In-line sample concentration by evaporation through porous hollow fibers and micromachined membranes embedded in microfluidic devices", "Electrophoresis 2016", 2016, pp. 463-471, vol. 37, Publisher: Wiley-VCH.
Zhou, S-F, et al., "Analysis of Autologous Platelet-Rich Plasma During Ascending and Transverse Aortic Arch Surgery", "Ann Thorac Surg", 2013, pp. 1525-1530, Publisher: Elsevier Inc.

* cited by examiner

A

B

A

B

| NAME | COUNT | Freq. Single Cells |
|---|---|---|
| negative | 165553 | 33.6 |
| CD62+ | 327046 | 66.4 |

| NAME | COUNT | Freq. Single Cells |
|---|---|---|
| negative | 275850 | 31.2 |
| CD62+ | 609250 | 68.8 |

| NAME | COUNT | Freq. Single Cells |
|---|---|---|
| negative | 427438 | 29.5 |
| CD62+ | 1023418 | 70.5 |

DEVICE AND METHOD FOR THE PREPARATION OF PLATELET RICH PLASMA

CROSS-REFERENCE TO RELATED APPLICATIONS

This application is a U.S. national phase under the provisions of 35 U.S.C. § 371 of International Patent Application No. PCT/EP18/62194 filed May 11, 2018, which in turn claims priority of European Patent Application No. EP17382271.9 filed May 12, 2017. The disclosures of International Patent Application No. PCT/EP18/62194 and European Patent Application No. EP17382271.9 are hereby incorporated herein by reference in their respective entireties, for all purposes.

FIELD OF THE INVENTION

The present invention relates to the field of microfluidics and regenerative medicine. In particular, the invention provides a device and method for the preparation of platelet rich plasma, and platelet rich plasma obtained by employing said device and method.

BACKGROUND OF THE INVENTION

In recent years, biological advanced therapies and regenerative medicine have become a promising alternative to conventional treatments. The use of Platelet Rich Plasma (PRP) is one of the technologies that has spread most and consolidated over several fields of medicine. Proof of this is the economic impact in the global market, where the technology was valued at $45 million in 2009, and $120 million by 2016.

PRP is a suite of autologous blood products in which platelets are found at higher concentrations than in blood. Once PRP is activated, plasma fibrinogen polymerizes into a three-dimensional transient fibrin scaffold, trapping several growth factors, microparticles, and other biomolecules released from the degranulation of platelets and plasma. Growth factors and biomolecules sequestered into the fibrin scaffold are released gradually and in a sustained manner as scaffold fibrinolysis occurs, hence PRP is highly suitable for enhancing and accelerating the natural process of tissue repair and ultimately reducing recovery times.

In particular, the released growth factors trigger biological processes aimed at repairing damaged tissue, for instance angiogenesis, chemotaxis, cell migration or proliferation by means of cell membrane signalling. Some types of growth factors circulate in plasma, e.g. Insulin-like Growth Factor (IGF) and Hepatocyte Growth Factor (HGF). IGF promotes wound healing, bone formation, myogenesis of striated muscle and keratynocite migration. HGF is involved in wound healing, and stands out for its antifibrotic and anti-inflammatory properties. Other growth factors are stored in platelets and are released when PRP is activated, e.g. transforming growth factor β1 (TGF-β1), which presents different effects depending on tissue type where it acts: cell migration, neovascularization or osteogenic differentiation; Vascular Endothelial Growth Factor (VEGF) is a key molecule involved in angiogenesis and organ homeostasis; Platelet-Derived Growth Factor (PDGF); basic Fibroblast Growth Factor (FGF-2); or Epithelial Growth Factor (EGF) among others.

Specific clinical practices into which PRP-based therapies have broken into are orthopaedics and sports medicine.

Proof of this are the increasing studies relating to pathologies such as osteoarthritis, tendinopathies or ligamentous injuries. As a result, a large number of PRP products have emerged in the market and, although these products are all generally labelled PRP, they present different properties, such as varying concentrations of platelets, presence or absence of leukocytes or activation manner. The device and method employed in the preparation of PRP has an important impact on said properties. Examples of commercially available systems for preparing PRP are Magellan (Arteriocyte Medtronic), ACP or Angel (Arthrex), PRGF-Endoret (BTI Biotechnology Institute), MTF (Cascade), Secquire (Pure PRP Emcyte), RegenKit (RegenLab), GPS (Zimmer Biomet), Ortho Pras (Proteal).

Despite the large number of PRP systems on the market, they are all based on the principle of centrifugation to concentrate platelets. This technique generates a concentration gradient according to the weight of the blood components and allows for isolating and concentrating the platelets. As a result of the rise in platelet concentration, platelet growth factors stored in these platelets are also increased. However, the speed of centrifugation employed in these methods cannot concentrate many non-platelet (extraplatelet) biomolecules found in plasma to the same degree as the aforementioned platelets or platelet growth factors. Obtaining said non-platelet molecules by centrifugation would involve very high speeds of centrifugation that are not compatible with cell viability or with everyday medical practice.

Although PRPs obtained by the above mentioned methods of the prior art are achieving promising results, a constant need exists for the development of new methodologies that are able to yield next generation PRPs that allow for more effective medical therapies.

SUMMARY OF THE INVENTION

The present inventors have now developed a microfluidic device which is capable of producing platelet rich plasma (PRP) products by a particular method of plasma concentration and dialysis.

The present inventors have found that through the use of said device and method, a PRP can be produced which has both concentrated levels of platelets (and therefore platelet growth factors) and of non-platelet biomolecules, especially of non-platelet growth factors.

Thus, in a first aspect, the present invention relates to a microfluidic device for evaporating and dialyzing plasma, comprising:

- a first platform (1) adapted for evaporating plasma comprising:
  - A first layer (2) comprising a first microchannel (3) formed on a first surface of said first layer (2);
  - A second layer (4) comprising a second microchannel (5) formed on a first surface of said second layer (4); and
  - A first permeable membrane (6) with a molecular-weight cutoff (MWCO) between 10 Dalton and 1000 kDalton, placed between the first and second layer (2, 4);

wherein the first surface of the first and second layers (2, 4) face each other and are in contact with the first permeable membrane (6);

wherein the first permeable membrane (6) covers the first and second microchannels (3, 5), such that plasma can flow through the first microchannel (3) and fluid can flow through the second microchannel (5);

wherein the first and second microchannels (3, 5) are spatially arranged with respect to each other such that molecules that evaporate from the first microchannel (3) and cross the first permeable membrane (6) are received in the second microchannel (5);

wherein the first microchannel (3) comprises a first inlet (7) for inputting plasma and a first outlet (8) for outputting plasma, and the second microchannel comprises a second inlet (9) for inputting fluid and a second outlet for outputting fluid (10);

a second platform (11) adapted for dialyzing plasma comprising:

A third layer (12) comprising a third microchannel (13) formed on a first surface of said third layer;

A fourth layer (14) comprising a fourth microchannel (15) formed on a first surface of said fourth layer; and A second permeable membrane (16) with a molecular-weight cutoff (MWCO) between 100 Dalton and 1000 kDalton, placed between the third and fourth layer (12, 14);

wherein the first surface of the third and fourth layers (12, 14) face each other and are in contact with the second permeable membrane (16);

wherein the second permeable membrane (16) covers the third and fourth microchannels (13, 15), such that plasma can flow through the third microchannel (13) and fluid can flow through the fourth microchannel (15);

wherein the third and fourth microchannels (13, 15) are spatially arranged with respect to each other such that molecules that diffuse from the third microchannel (13) and across the second permeable membrane (16) are received in the fourth microchannel (15);

wherein the third microchannel (13) comprises a third inlet (17) for inputting plasma and a third outlet (18) for outputting plasma, and the fourth microchannel (15) comprises a fourth inlet (19) for inputting fluid and a fourth outlet (20) for outputting fluid;

wherein the first outlet (8) is in fluid communication with the third inlet (17), or the third outlet (18) is in fluid communication with the first inlet (7).

In a second aspect, the invention is directed to a method for the preparation of platelet-rich plasma (PRP) enriched in non-platelet biomolecules, comprising the following steps:

a) Providing a device as described in the first aspect of the invention;

b) Providing a plasma sample;

c) Inputting the plasma sample into the first microchannel (3); and flowing the plasma sample through the first microchannel (3) to evaporate the plasma sample;

d) Flowing the plasma sample flowed through the first microchannel (3) through the third microchannel (13) to dialyse the plasma sample; and e) Outputting the plasma sample from the third microchannel (13), or alternatively c) Inputting the plasma sample into the third microchannel (13); and flowing the plasma sample through the third microchannel (13) to dialyse the plasma sample;

d) Flowing the plasma sample flowed through the third microchannel (13) through the first microchannel (3) to evaporate the plasma sample; and e) Outputting the plasma sample from the first microchannel (3).

The present inventors have unexpectedly found that the PRP product obtained by the method of the second aspect of the invention presents improved regenerative properties when compared to PRP products prepared by the above mentioned conventional methodologies.

Thus, in a third aspect, the invention refers to a PRP product obtained by the method of the present invention.

In a further aspect, the invention relates to the PRP product of the present invention for use in regenerative medicine.

In yet another aspect, the invention relates to the cosmetic use of PRP product of the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

The device of the present invention is a microfluidic device. The term microfluidic device as used herein is a device comprising channels through which moving fluid is directed and wherein one or more of the dimensions of said channels are in the micrometre range. Channels with such dimensions are herein referred to as "microchannels". Preferably, the microchannels are between 1 μm and 50 mm in width and/or in depth, wherein either the depth is less than 10 mm and/or the width is less than 1 mm. Preferably, the microchannels are up to 500 mm in length, preferably from 0.1 mm to 500 mm in length. The dimensions of the microchannels will depend on the intended purpose of the device, and are usually a compromise between greater dimensions which provide larger surface areas suitable for efficient evaporation and/or dialysis, and smaller dimensions which are suitable for making the device as much portable as possible.

The device of the invention is easy to use, cheap to fabricate and operate, and enables the automatization of the whole method of the invention, and can be easily disposed of. The device of the invention thus enables sample processing by nonprofessional personnel, improving safety to the user and minimising human errors. The device of the present invention is further ideal for portable and in-situ biomedical devices, eliminating the need to use outside labs.

The device of the present invention comprises at least two platforms: an evaporation platform and a dialysis platform. In the context of the present invention, a platform refers to an individual, self-contained part of the device designed to perform a particular task. In the device of the present invention, each of the two platforms is in itself a microfluidic device. The first platform is a microfluidic device configured for evaporating plasma. The second platform is a microfluidic device configured for dialysing plasma.

Each platform according to the present invention comprises three main components: two layers, each comprising at least one microchannel, and a permeable membrane.

The microchannels are formed on a first surface of each layer and do not penetrate the entire depth of the layer. When each layer is taken in isolation, i.e. prior to their assembly with the membrane, the section of the microchannels is not a closed trajectory. The inside of the microchannels can therefore be accessed from the outside.

The microchannels are formed on the first surface of the layers by any means known in the art, e.g. by drilling such as CNC micromilling; engraving; carving; lithographic means such as etching; laser ablation, hot-embossing or injection moulding techniques.

Figure 1:
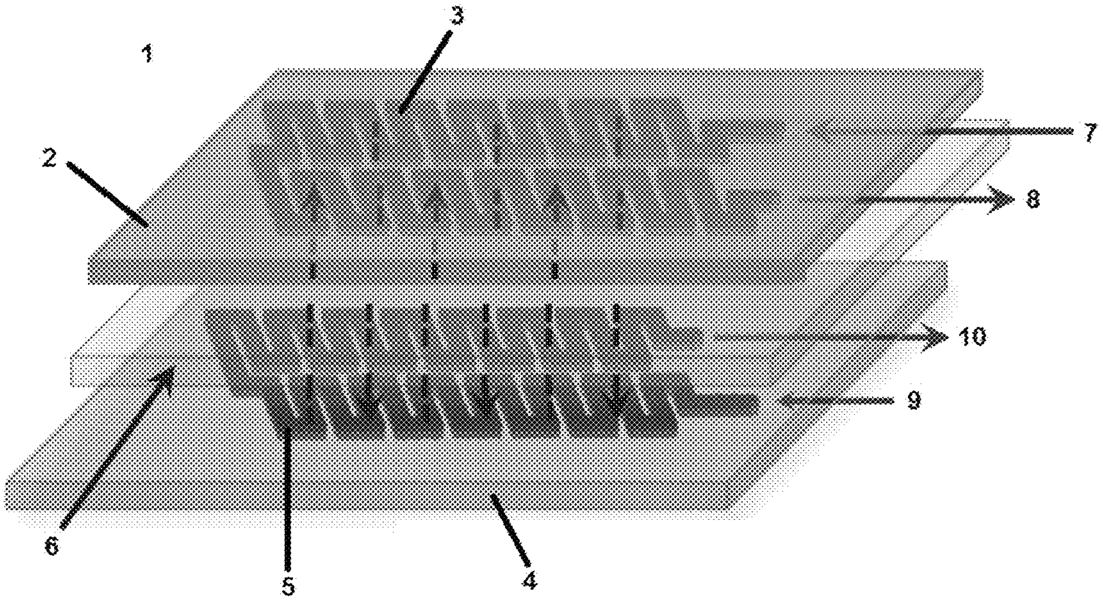
FIG. 1. Evaporation platform according to the device of the present invention; 1A) graphic representation; 1B) real image.
Figure 1:
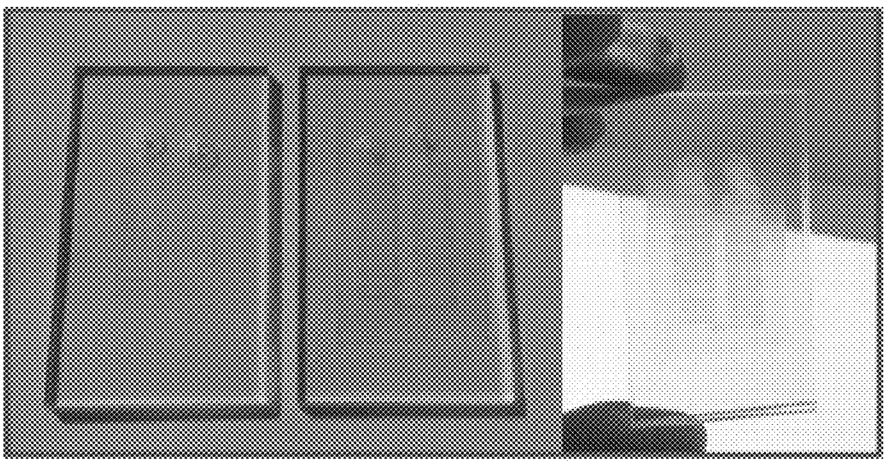
Figure 2:
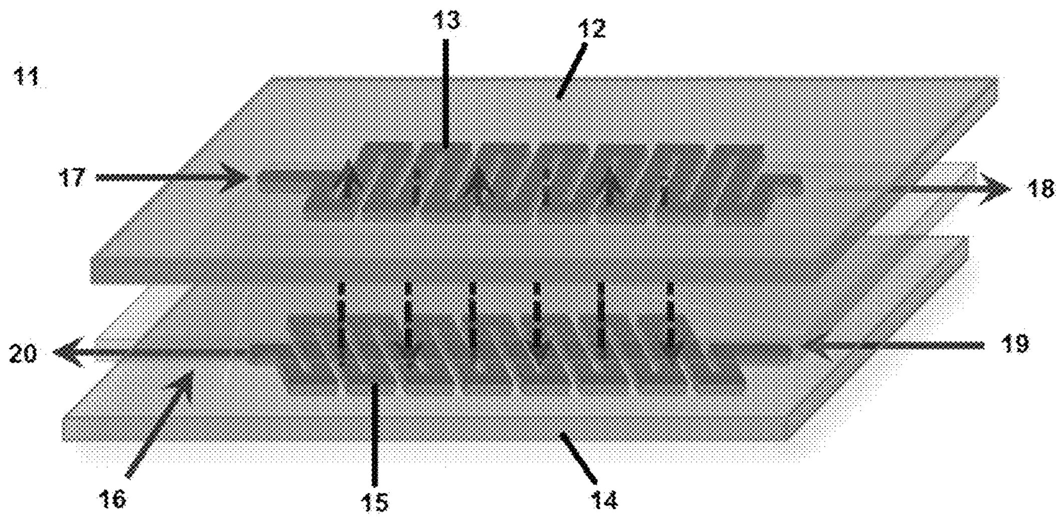
FIG. 2. Dialysis platform according to the device of the present invention; 2A) graphic representation; 2B) real image.
Figure 2:
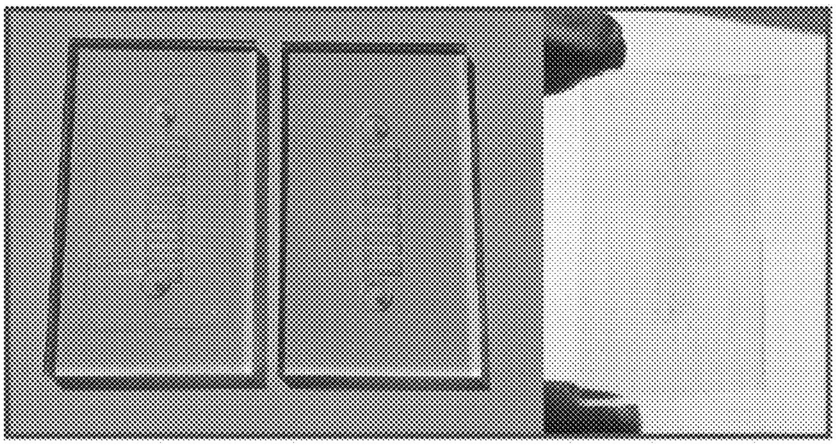

The first surface of each layer onto which the microchannels are formed is generally that with the greatest area, as seen in FIGS. 1 and 2.

The layers may be any shape suitable for their function. Preferably, the layers are rectangular.

The size of the layers (and other device components) will depend on the intended purpose of the device. The layers can be between 0.005 and 100 mm thick. In a preferred embodiment, the layers are between 0.1 and 4 mm thick, more preferably 2 mm.

The layers may each independently be made of a material selected from a metallic, ceramic, glass, or polymeric material.

Preferably, the material is optically transparent, in order to facilitate observation and monitoring of fluids moving through the microfluidic device by the naked eye.

Preferably, the material is a polymeric material. Examples of polymeric materials are polydimethylsiloxane (PDMS), polymethylmethacrylate (PMMA), polycarbonate (PC), polystyrene (PS), polypropylene (PP), polyethylene (PE), high density polyethylene (HDPE), polyimide, cyclic olefin copolymer (COC), cyclic olefin polymers (COP), polyethylene terephthalate (PET), epoxy resins, a non-stick material such as teflon (PTFE), a variety of photoresists such as SU8 or any other thick film photoresist, or a combination of these materials. Preferably, the polymeric material is PP, PE, COC, COP or PMMA, and in particular it is PMMA.

Preferably, all the layers of a same platform are made of the same material. In a particular embodiment, all the layers in the device are made of the same material.

The microchannels formed on the first surface of each layer may be linear in shape, or they may have any other configuration required for device function, including a curved configuration, spiral configuration, angular configuration (e.g. perpendicular), or combinations thereof. Preferably, the axis of fluid flow through the microchannels lies within a single horizontal plane.

Amongst other factors mentioned further below, the length of the microchannel through which plasma runs will determine the extent of evaporation or dialysis that takes place at each respective platform. Thus, the length of the microchannel is usually preferably maximised. Preferably, the length of the microchannel occupies at least 20%, at least 35%, at least 50% or at least 65% of the first surface of the corresponding layer.

In some embodiments, two or more microchannels may converge into a single microchannel. Such a design may be incorporated into a layer, for example, to combine two or more liquids within a microfluidic device. Similarly, two or more microchannels may diverge from a single microchannel. Microchannels may intersect in a variety of fashions as required for device performance, forming Y-shaped intersections, T-shaped intersections, and crosses.

In an embodiment, the microchannels comprise components designed to mix, react, and/or analyze samples from the flowing plasma, usually in volumes of less than one milliliter. Examples of such components are chambers, microwells, micropillars, trenches, vias, holes, cavities, grooves, slanted grooves, mesa, or combinations thereof.

The term "fluid" as used herein refers to a gas or a liquid.

The permeable membrane is a membrane permeable to some plasma components, but not others. Discrimination is carried out based on the molecular weight of the plasma components. Filtration membranes are produced with and characterised by differing molecular-weight cutoffs (MWCOs) measured in Dalton. The MWCO of a membrane refers to the smallest molecular mass (in Dalton) of a molecule that will not effectively diffuse across the membrane. Typically, this means the smallest molecular mass that is retained by greater than 90% upon extended exposure (e.g. overnight or 12 h) to the membrane.

Membrane manufacturers specify MWCOs of their membranes. The MWCO value of a membrane may however also be experimentally determined by a person skilled in the art by subjecting the membrane to compounds of known molecular weight and monitoring permeation. This can be done by following the American Society for Testing and Materials (ASTM) method E1343-90(2001).

The membranes used in the device of the present invention are commercially available from suppliers such as Carl Roth (e.g. Nadir series), ThermoFischer Scientific (e.g. Fisherbrand, SnakeSkin, Biodesign series), Spectrum Laboratories (e.g. Spectra/Por series), Interchim (e.g. CelluSep series) or Sigma Aldrich.

The membranes used in the device of the present invention may be hydrophilic or hydrophobic. The membranes may be made of an organic or inorganic material, or of a mixture thereof. The inorganic material is preferably a ceramic material, such as aluminium or titanium oxides, nitrides or carbides. However, the membrane is preferably made of an organic material. The organic material is preferably a natural or synthetic polymer such as cellulose or ester derivatives thereof such as cellulose acetate, nitrocellulose, polysulfone, polyimide, polyimide, polyethylene, polypropylene, polytetrafluoroethylene, polyvinylidene fluoride, or polyvinylchloride. Preferably, the organic material is cellulose. More preferably, the cellulose is regenerated cellulose.

As used herein, the term "regenerated cellulose" refers to manmade cellulose material obtained by chemical treatment of natural cellulose to form a chemical derivative or intermediate compound and subsequent decomposition of the derivative or intermediate to regenerate the cellulose. Examples of regenerated cellulose are rayon, lyocell, viscose, or any combination thereof.

Each platform may be in any suitable shape. For example each platform may be in the form of substantially flat or flat sheets (wherein each of the layers and the permeable membrane is a sheet) or in the form of a concentric tube (wherein each of the layers and the permeable membrane is a circle). In a preferred embodiment it is in the form of substantially flat or flat sheets. As used herein, "substantially flat" is intended to mean a plane that may be at an angle of between +5 degrees and −5 degrees to the horizontal.

The membrane is in contact with (sandwiched by) the two layers, with the surface of the layers onto which the microchannels are formed facing the membrane as well as each other, as can be observed in FIGS. 1 and 2. The layers and the membrane may have different sizes or shapes, provided that the membrane is able to cover the full length of the microchannels formed on the first surface of the layers with which it is in contact. The full covering of the microchannels by the membrane is necessary to prevent any escape of fluid from the microchannels at said first surfaces.

Once the layers and the membrane have been assembled to form the core of each platform, they must be held in place. This can be achieved by any means known in the art. For instance, a non-permanent holding in place may be desirable where the platform can be directly accessed from the outside. A method of non-permanent assembly is for instance encasing, e.g. in a holder which is preferably optically transparent in order to facilitate observation and monitoring of fluids moving through the microfluidic device by the naked eye. Said non-permanent assemblies allow replacing the different components of the platform, in particular a layer and/or the membrane, thus making the device more versatile in nature. However, a permanent assembly may be desirable where the platform is not directly accessible from the outside, e.g. where the platform is comprised within an apparatus (accessing the platform requires for instance disassembling some part of the apparatus) or where the same kind of sample is always fed to the platform and versatility is not important. Examples of methods of permanent assembly are sealing, e.g. by means of an adhesive, or embedding (e.g. in the apparatus) e.g. by means of temperature or/and pressure treatment.

The device of the invention preferably comprises means for running and controlling the flow of plasma and/or the fluids through the microchannels, such as pumps or valves, which may be manual or automated. In a preferred embodiment, said means are a syringe pump.

The terms "running", "flowing" and "passing" fluid through a microchannel are herein used interchangeably.

Evaporation Platform

As mentioned above, the device of the present invention comprises an evaporation platform, also referred to herein as concentration platform. The purpose of this platform is to concentrate plasma by evaporation. Evaporation is a type of vaporization of a liquid that occurs from the surface of a liquid into a gaseous phase that is not saturated with the evaporating substance.

Plasma is run through the at least one microchannel of one of the two layers forming the platform, whilst a fluid is held in, preferably run through, the at least one microchannel of the other layer forming the platform. The layer and the at least one microchannel through which plasma is run are herein respectively referred to as the first layer and first microchannel. The layer and the at least one microchannel wherein fluid is held or through which the fluid is run are herein respectively referred to as the second layer and second microchannel. As mentioned further above, the layers are separated by a permeable membrane which also serves to cover the microchannels formed on the first surface of the first and second layers.

By running fluid through the second microchannel, gas molecules that evaporate from the plasma in the first microchannel and diffuse through the permeable membrane and enter the fluid stream in the second microchannel are carried away by the fluid, thus ensuring no build-up of evaporated molecules at the second microchannel takes place.

The dimensions of the first microchannel or microchannels are preferably as follows. The width of the microchannel is preferably between 30 000 and 50 μm, and more preferably between 2000 and 250 μm, most preferably about 1000 μm; the depth of the microchannel is preferably between 1 and 2000 μm, more preferably between 50 and 300 μm, and most preferably about 150 μm; the length of the microchannel is preferably between 1 and 500 mm, more preferably between 100 and 300 mm, most preferably 230 mm.

The dimensions of the second microchannel or microchannels are preferably as follows. The width of the microchannel is preferably between 30 000 and 50 μm, and more preferably between 2000 and 250 μm, most preferably about 1000 μm; the depth of the microchannel is preferably between 1 and 2000 μm, more preferably between 50 and 300 μm, and most preferably about 150 μm; the length of the microchannel is preferably between 1 and 500 mm, more preferably between 100 and 300 mm, most preferably 230 mm.

As used herein, the term "about" refers to a slight variation of the value specified, preferably within 10% of the value specified.

The first layer comprises an inlet for inputting plasma into the first microchannel and an outlet for outputting the plasma that has undergone evaporation from the first microchannel. The second layer preferably comprises an inlet for inputting a fluid into the second microchannel, and an outlet for outputting from the second microchannel fluid carrying the molecules that have evaporated from the plasma and crossed the membrane. Inlets and outlets may herein be generally referred to as ports. If the fluid in the second microchannel is stationary, then the inlet and outlet of the second microchannel are provided with opening and closing means, so that the microchannel can be closed after fluid has been inserted therein, and reopened when emptying of the microchannel or the introduction of fresh fluid is desired.

The term "inlet", as used herein, refers to a terminal opening of a microchannel wherein a fluid (including plasma) enters the microchannel. For example, a microchannel inlet may be fluidly connected to a loading deck wherein an introduced fluid passes through the loading deck and into the microchannel. Alternatively, the inlet can be fluidly connected to the outlet of a layer of a different platform lying further upstream in the flow of fluid.

The term "outlet", as used herein, refers to a terminal opening of a microchannel wherein a fluid (including plasma) exits the microchannel. For example, a microchannel outlet may be fluidly connected to a collection module. Alternatively, the outlet can be fluidly connected to the inlet of a layer of a different platform lying further downstream in the flow of fluid.

The ports of the microchannels can be arranged anywhere on the layers. It is to be understood that where more than one microchannel or where converging or diverging microchannels are formed on a layer, then more than one inlet or outlet can be arranged.

In a preferred embodiment, the inlet/outlet ports of the first layer are placed de-aligned with respect to the inlet/outlet ports of the second layer (along a layer-membrane-layer axis intersecting these components perpendicularly), to avoid any possible membrane break caused by the different flows (plasma and fluid flow). In other words, no port of the first layer should lie immediately above or beneath of any second layer port (along a layer-membrane-layer axis intersecting these components perpendicularly).

In a preferred embodiment, the first microchannel or microchannels are spatially arranged with respect to the second microchannel or microchannels such that molecules that evaporate from the first microchannel and cross the permeable membrane are received in the second microchannel. Preferably, at least 50% of the path formed by the first microchannel or microchannels on the first layer overlaps with the path formed by the second microchannel or microchannels on the second layer (along a layer-membrane-layer axis intersecting these components perpendicularly). More preferably, the overlap is at least 70%, and more preferably it is at least 90%.

In an embodiment, the surface of the first layer onto which the first microchannel is formed is between 50 and 1000 $mm^2$ large, preferably between 100 and 500 $mm^2$ large, more preferably between 200 and 400 $mm^2$ large. In a particular embodiment it is about 230 $mm^2$ large.

The permeable membrane of the evaporation platform has a MWCO between 10 Da and 1000 kDa, more preferably between 4.5 kDa and 1000 kDa, even more preferably between 4.5 kDa and 100 kDa, and most preferably between 10 and 20 kDa.

Alternatively, the permeable membrane of the evaporation platform has an average pore size of from 1 to 10 000 Å, more preferably from 1 to 1000 Å, even more preferably from 1 to 100 Å, and most preferably from 25 to 30 Å.

Evaporation may be enhanced by heating the plasma that is run through the first microchannel. A slight increase of the plasma temperature leads to greater kinetic energy of the water molecules at the plasma surface, and therefore to a faster rate of evaporation. The temperature of the plasma should not be so high so as to negatively impact on the functionality of platelets and other biomolecules in plasma which are to be retained in the final plasma product. Since evaporation takes place in an enclosed area, the escaping molecules accumulate as a vapor above the plasma. The fluid stream supplied through the second layer makes the concentration of vapor less likely to go up with time, thus encouraging faster evaporation.

Heating of the plasma sample may be achieved by arranging means for heating the plasma in the device of the invention. The means may be means for heating the plasma prior to inputting the plasma in the first microchannel or means for heating the plasma as it runs through the first microchannel. When means for heating the plasma as it runs through the first microchannel are used, any means for heating the first microchannel, the first layer, or the first platform altogether are suitable.

The means for heating the plasma may be external to the first platform (i.e. non-integrated) or integrated in the first platform. Suitable external heating means are hot plates or macroscopic Peltier devices. Examples of integrated heating means are micro-Peltier components, Joule heaters, Microwave heaters, endothermal chemical reaction heaters, or wire or laser heaters. Means for heating microfluidic devices are extensively reviewed in Miralles et al., Diagnostics, 2013, 3, 33-67, the contents of which are included herein by reference.

When means for heating plasma are arranged, then means for determining the temperature of the plasma may also preferably be arranged in the device of the invention. Preferably, the means for determining the temperature of the plasma comprise one or more temperature sensors. These temperature sensors may be sensors placed within the microchannel or within any other device component through which the plasma flows (e.g. at inlet/outlet ports or channels connecting different platforms), or sensors external to the microchannel. Preferably, the one or more sensors within the microchannel are passivated to prevent direct contact with plasma. In an embodiment, the passivation materials comprise one or more of the following: glass, silicon dioxide, silicon nitride, silicon, polysilicon, parylene, polyimide, Kapton, or benzocyclobutene. Preferably, the one or more external sensors have a thermal capacitance that is matched to that of the measured temperature zone on the microfluidic device.

When means for heating plasma are arranged, then means for cooling plasma may also be arranged. This might be useful for cooling the plasma when undesired heat peaks occur, e.g. due to non-uniform heating of the plasma, and thus in order to prevent damage to biomolecules contained in the plasma. The arrangement of cooling means is also useful when a fine-tuning of the plasma temperature is desired.

The means for heating and/or cooling plasma, and/or the means for determining the temperature of the plasma are preferably microelectromechanical means.

Evaporation at the first platform may also be enhanced by running the plasma in the first microchannel or microchannels, and the fluid in the second microchannel or microchannels, in opposite directions. Thus, in a preferred embodiment, the means for running plasma through the first microchannel or microchannels are configured to run plasma in a first direction, and the means for running fluid through the second microchannel or microchannels are configured to run the fluid in a second direction opposed to the first direction. In a preferred embodiment, the means for running plasma through the first microchannel and/or through the second microchannel are means configured for running plasma through the microchannel in both directions, i.e. in a reversible manner.

Dialysis Platform

As mentioned above, the device of the present invention comprises a dialysis platform. The purpose of this platform is to remove plasma components in order to enrich the remaining plasma in platelets and non-platelet biomolecules, particularly growth factors. Dialysis refers to the diffusion of molecules in the plasma across a selectively permeable membrane (the platform membrane) against a concentration gradient in an effort to achieve equilibrium. While small plasma molecules pass through the membrane larger plasma molecules are "trapped" in the plasma. The dialysis platform also serves to remove electrolytes from the plasma, which is important because platelets in the plasma end product may not become activated to release their growth factors if electrolyte concentration in the dialysed plasma is too high.

Plasma is run through the at least one microchannel of one of the two layers forming the platform, whilst a fluid is held in, preferably run through, the at least one microchannel of the other layer forming the platform. The layer and the at least one microchannel through which plasma is run are herein respectively referred to as the third layer and third microchannel. The layer and the at least one microchannel wherein the fluid is held or through which the fluid is run are herein respectively referred to as the fourth layer and fourth microchannel. As mentioned further above, the layers are separated by a permeable membrane which also serves to cover the microchannels formed on the first surface of the third and fourth layers.

By continuously running fluid through the fourth microchannel, the build-up in the fourth microchannel of the smaller plasma molecules that have diffused out of the plasma in the third microchannel, is prevented. Thus, the gradient across the membrane never reaches equilibrium and there is always a strong driving force present for smaller plasma molecules to continuously pull away from the plasma, thus efficiently enriching the plasma in the larger molecules.

The dimensions of the third microchannel or microchannels are preferably as follows. The width of the microchannel is preferably between 30 000 and 50 μm, and more preferably between 2000 and 250 μm, most preferably about 1000 μm; the depth of the microchannel is preferably between 1 and 2000 μm, more preferably between 50 and 300 μm, and most preferably about 150 μm; the length of the microchannel is preferably between 1 and 500 mm, more preferably between 100 and 300 mm, most preferably 115 mm.

The dimensions of the fourth microchannel or microchannels are preferably as follows. The width of the microchannel is preferably between 30 000 and 50 μm, and more preferably between 2000 and 250 μm, most preferably about 1000 μm; the depth of the microchannel is preferably between 1 and 2000 μm, more preferably between 50 and 300 μm, and most preferably about 150 μm; the length of the microchannel is preferably between 1 and 500 mm, more preferably between 100 and 300 mm, most preferably 115 mm.

The third layer comprises an inlet for inputting plasma into the third microchannel and an outlet for outputting dialysed plasma from the third microchannel. The fourth layer preferably comprises an inlet for inputting a fluid into the fourth microchannel, and an outlet for outputting from the fourth microchannel fluid carrying the plasma molecules that have diffused from the plasma across the membrane. If the fluid in the fourth microchannel is stationary, then the inlet and outlet of the fourth microchannel are provided with opening and closing means, so that the microchannel can be closed after fluid has been inserted therein, and reopened when emptying of the microchannel or the introduction of fresh fluid is desired.

It is to be understood that where more than one microchannel or where converging or diverging microchannels are formed on a layer, then more than one inlet or outlet can be arranged.

In a preferred embodiment, the inlet/outlet ports of the third layer are placed de-aligned with respect to the inlet/outlet ports of the fourth layer (along a layer-membrane-layer axis intersecting these components perpendicularly), to avoid any possible membrane break caused by the different flows (plasma and fluid flow). In other words, no port of the third layer can lie immediately above or beneath of any fourth layer port (along a layer-membrane-layer axis intersecting these components perpendicularly).

In a preferred embodiment, the third microchannel or microchannels are spatially arranged with respect to the fourth microchannel or microchannels such that molecules that diffuse from the third microchannel and cross the permeable membrane are received in the fourth microchannel. Preferably, at least 50% of the path formed by the third microchannel or microchannels on the third layer overlaps with the path formed by the fourth microchannel or microchannels on the fourth layer (along a layer-membrane-layer axis intersecting these components perpendicularly). More preferably, the overlap is at least 70%, and more preferably it is at least 90%.

The permeable membrane of the dialysis platform has a MWCO between 100 Da and 1000 kDa, more preferably between 100 Da and 100 kDa, even more preferably between 100 Da and 10 kDa, and most preferably of about 1 kDa.

Alternatively, the permeable membrane of the evaporation platform has an average pore size of from 1 to 10 000 Å, more preferably from 1 to 1000 Å, even more preferably from 1 to 100 Å, and most preferably from 1 to 5 Å.

Dialysis may also be enhanced by running the plasma in the third microchannel or microchannels, and the fluid in the fourth microchannel or microchannels, in opposite directions. Thus, in a preferred embodiment, the means for running plasma through the third microchannel or microchannels are configured to run plasma in a first direction, and the means for running fluid through the fourth microchannel or microchannels are configured to run the fluid in a second direction opposed to the first direction. In a preferred embodiment, the means for running plasma through the third microchannel and/or through the fourth microchannel are means configured for running plasma through the microchannel in both directions, i.e. in a reversible manner.

Platform Inter-Relationship

Plasma may be firstly evaporated in the evaporation platform, and then dialyzed in the dialysis platform, or vice versa. The sequence in which plasma is treated will determine the relative arrangement of the two platforms in the device. Thus, if plasma is firstly evaporated and then dialysed, the outlet of the first microchannel is connected to—more particularly in fluid communication with—the inlet of the third microchannel. If plasma is however firstly dialysed and then evaporated, the outlet of the third microchannel is connected to—more particularly in fluid communication with—the inlet of the first microchannel. Preferably, the plasma is firstly evaporated in the evaporation platform, and then dialyzed in the dialysis platform, and therefore in a preferred arrangement, the outlet of the first microchannel is connected to the inlet of the third microchannel.

The expressions "fluidic communication" or "fluidly connected" or similar refer to any configuration of microchannels and/or microdevice components that allow for the uninterrupted movement of fluid without passing through a platform. Means for arranging parts of the device in fluidic communication are well known in the art, e.g. tubing such as polytetrafluoroethylene (PTFE) tubing. Said means for fluidically communicating the different components of the device may be reinforced with sealing means such as toric joints so as to minimize the possibility of fluid escaping from inbetween the different components of the device.

The fluid employed in the evaporation platform to remove molecules that have pulled away out of the plasma is generally a different one to the fluid employed for the same purpose in the dialysis platform. Nevertheless, in a particular embodiment, the same fluid is employed, and thus, the second and fourth microchannels may be in fluid communication with each other in the same manner as the first and third microchannels are.

The means for running and controlling the flow of plasma and/or fluid through the microchannels may be arranged anywhere in the device suitable for this purpose, but they are preferably arranged in direct fluid communication with (upstream from) the inlet port of the microchannel which comes first (i.e. is most upstream) in the plasma/fluid flow direction. Wherever microchannels are in fluid communication with other microchannels, one set of means for running and controlling the flow of the plasma or fluid plasma through said fluid-connected microchannels can suffice.

The second and fourth microchannels are not usually in fluid communication with each other. When this is the case, means for running and controlling the flow of fluid through these microchannels are arranged at each of these microchannels.

The plasma outputted from the device of the invention, and more particularly from the microchannel of the platform of said device lying further downstream in the flow of plasma, may be recirculated back into the same device, and more particularly into the microchannel of the platform of said device lying further upstream in the flow of plasma, in order to repeatedly evaporate and dialyse the same plasma sample. Thus, the plasma outputted from the first or third microchannel may respectively be recirculated back into the third or first microchannel.

Thus, in a preferred embodiment, the first or third layer comprises means for respectively recirculating plasma outputted from the first or third microchannel back into the third or first microchannel. This may be provided in the form of a multiway switch, which is placed at the outlet of the microchannel lying further downstream in the flow of plasma. The switch may be operated manually or in an automated fashion. The switch is configured to either forward the plasma to a collection module or to a further device, such as a device according to the present invention, or to direct the plasma back into the microchannel lying further upstream in the flow of plasma, preferably through the inlet of said upstream microchannel.

In a further embodiment, repeated evaporation and dialysis is achieved by running the plasma through more than one device according to the present invention. Thus, plasma is evaporated and dialysed at a first device according to the present invention, said first device being in fluid communication with a further device according to the present invention, such that plasma outputted from the first device can be inputted into the second device for further evaporation and dialysis. Any desirable number of devices according to the present invention may be placed in series in order to run plasma through said devices and afford further evaporation and dialysis.

The device of the invention preferably comprises means for collecting the plasma and/or fluid outputted from the microchannels. In the case of the second and fourth microchannels, this is usually a waste container. However, if fluids which are expensive or limited in amount are employed, the fluid may be inserted in these microchannels and kept stationary therein, or means for recirculating the fluid such as a multiway switch may be arranged at the outlet of the corresponding microchannels configured for directing the fluid back into the microchannel from which it exited, preferably through the microchannel inlet.

Method for the Preparation of PRP

Another aspect of the invention refers to a method for the preparation of platelet-rich plasma (PRP) also enriched in non-platelet biomolecules, in particular in non-platelet plasmatic growth factors.

The method of the invention is carried out in a device according to the invention as described in any of the above embodiments. The amount of both platelets and non-platelet biomolecules, in particular non-platelet plasmatic growth factors, in a particular plasma sample can thus advantageously be increased by selective evaporation and dialysis. This is not possible with methods for preparing PRP based solely on centrifugation, as was explained further above.

The method comprises, in a first step, inputting plasma into the first or third microchannel, whichever is placed upstream from the other; and flowing the plasma through the microchannel to evaporate the plasma sample (in the case of the first microchannel) or dialyse the plasma (in the case of the third microchannel).

Figure 3:
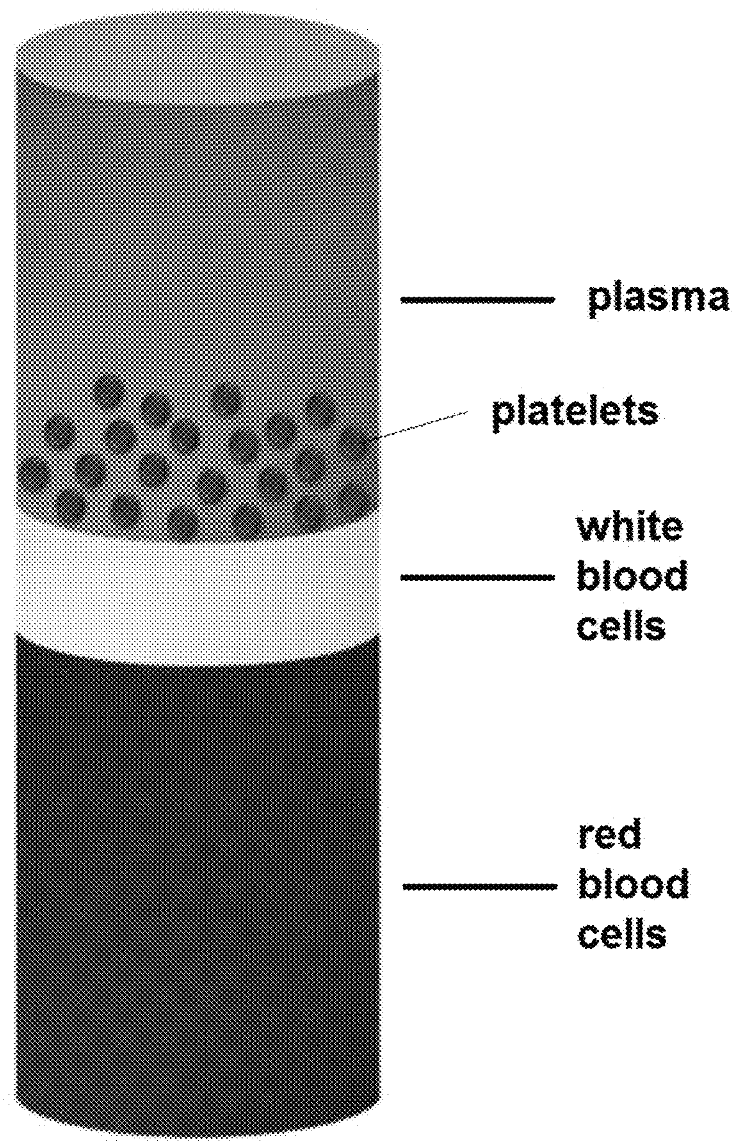
FIG. 3. Whole blood components after centrifugation.

The plasma inputted in the microchannel (or generally in the device) of the invention can be any kind of plasma. The term "plasma" as used herein refers to the fluid portion of whole blood which contains neither red blood cells nor white blood cells (or contains very low amounts thereof, such as 5% by weight or lower of each with respect to the total plasma weight), but does contain platelets (or contains an amount of platelets of over 5% by weight with respect to the total plasma weight) (see FIG. 3). This definition of plasma may also be referred to as "plasma comprising platelets" where it is strictly interpreted that the term plasma cannot include platelets. Plasma may be obtained from a variety of animal sources, including human sources. The inputted plasma may be plasma isolated from whole blood without any post-isolation processing of the plasma, and in particular without any platelet enrichment, or the inputted plasma may also advantageously be plasma which has been further processed into other plasma products after isolation from whole blood, for instance into a platelet-rich plasma (PRP). The device and method of the invention produce plasma which is enriched both in platelets and in non-platelet biomolecules. Thus, in the particular embodiment wherein the inputted plasma is PRP, the device and method of the invention can serve to concentrate non-platelet biomolecules in said PRP.

In another embodiment the plasma inputted in the microchannel (or generally in the device) is a plasma as defined above that does comprise white blood cells, or rather comprises an amount of white blood cells of over 5% by weight with respect to the total plasma weight. The white blood cells remain in the plasma after evaporation and dialysis. The inclusion of white blood cells is advantageous for the breakdown and removal of dead tissue that might be delaying healing and recovery, as well as for helping prevent infection, at the site of injury.

The platelets in plasma inputted in the device of the invention may be degranulated or, in a preferred embodiment, the platelets in plasma inputted in the device of the invention are not degranulated.

As used herein, "platelet rich plasma" refers to plasma which has undergone a process increasing its concentration of platelets. In a preferred embodiment, it refers to plasma which has undergone a process increasing the concentration of platelets thereof by at least 1.2 fold, at least 1.4 fold or at least doubling the concentration of platelets thereof.

As used herein, "non-platelet biomolecules" refers to biomolecules not stored in platelets. Preferably, "non-platelet biomolecules" refers to plasmatic biomolecules. Preferably, "non-platelet biomolecules" refers to growth factors. Preferably, the term "non-platelet biomolecules" refers to biomolecules which cannot be concentrated by centrifugation techniques without damaging platelets or the biomolecules themselves upon said centrifugation. Concentration refers to at least a 1.2 fold increase in the concentration of the biomolecule, preferably at least a 1.4 fold increase, or more preferably to at least a doubling in the concentration of the biomolecule concentration.

As used herein, "plasma enriched in non-platelet biomolecules" refers to plasma which has undergone a process increasing its concentration of non-platelet biomolecules. In a preferred embodiment, it refers to plasma which has undergone a process increasing the concentration of non-platelet biomolecules thereof by at least 1.2 fold, at least 1.4 fold or at least doubling the concentration of non-platelet biomolecules thereof.

In a second step, the concentrated or dialysed plasma is respectively flown through the third or first microchannel in order to dialyse or concentrate the plasma.

In a third step, the concentrated and dialysed plasma is outputted from the platform lying most downstream in the flow of plasma, and in a final step said outputted plasma is collected.

Figure 4:
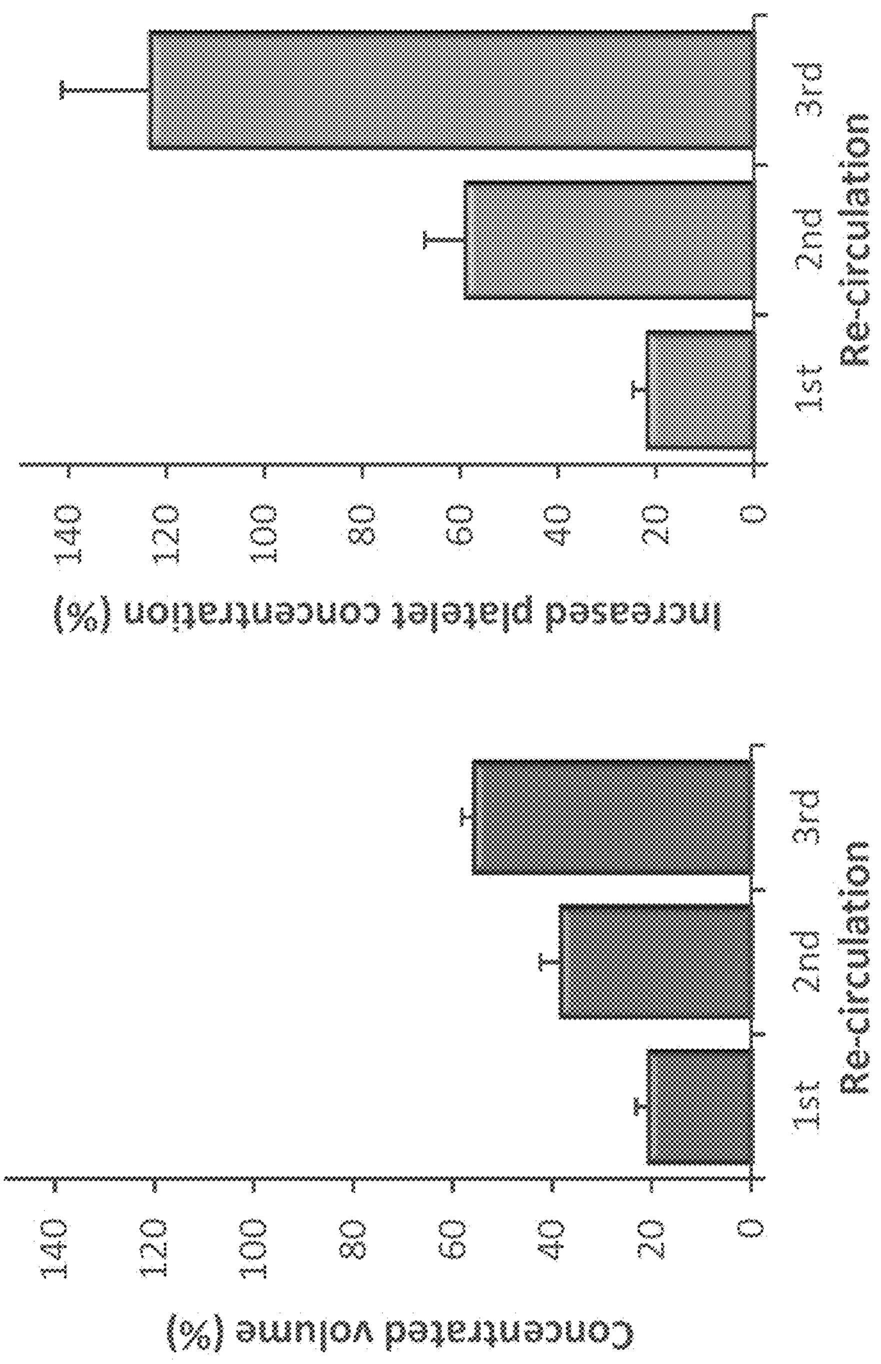
FIG. 4. Effect of recirculation of plasma through evaporation platform on plasma volume (left) and platelet concentration (right).

In a preferred embodiment, the plasma is recirculated through the evaporation and dialysis platform for further evaporation and dialysis. This is achieved by recirculating the plasma outputted from the third microchannel back into the first microchannel, or by recirculating the plasma outputted from the first microchannel back into the third microchannel. The present inventors have surprisingly found that the efficiency of platelet concentration increases exponentially upon recirculation of the plasma sample, even though the reduction in plasma volume shows a linear behaviour. This is shown in FIG. 4.

In a particularly preferred embodiment, plasma is first concentrated and then dialysed.

In a preferred embodiment, the method of the invention is carried out with the device of the invention oriented in space such that the second and fourth layers lie beneath the first and third layers, respectively. By the effect of gravity, diffusion of molecules from the first microchannel into the second, and from the third microchannel into the fourth is enhanced.

In a preferred embodiment, the plasma is heated prior to inputting it into the first microchannel, or in a different embodiment as it is run through the first microchannel.

Preferably, the plasma is heated up to 50° C., preferably up to 37° C. more preferably to between room temperature (21° C.) and 37° C., even more preferably to between 35° C. and 37° C. It has been found that over 37° C., operation of the device is limited, since the higher degree of evaporation of the plasma produces frequent obstructions in the microchannels. Moreover, over this temperature the functionality of proteins and platelets can become compromised. Therefore, preferably the plasma is heated at a temperature not higher than 37° C. The means for heating plasma, such as a hot plate, may be at a higher temperature thus allowing for a rapid heating of the plasma to the above stated temperature.

In a preferred embodiment, the plasma is run through the first microchannel at a rate of from 0.001 mL/min to 10 mL/min, more preferably at a rate of from 0.01 mL/min to 0.10 mL/min, more preferably at a rate of from 0.02 mL/min to 0.04 mL/min, and most preferably at a rate of about 0.04 mL/min.

In a preferred embodiment, the fluid run through the second microchannel is a gas. In a preferred embodiment, the gas is run through the second microchannel at a pressure of 0.001 to 2.0 bar.

Preferably, the gas is an inert gas. Preferably, the inert gas is selected from the group consisting of $N_2$, He, Ar, $H_2$, and a combination thereof, and it is most preferably $N_2$. Preferably, the gas is a dry gas. Dry gas, as used herein, refers to a gas having less than or equal to ten parts-per-million by volume moisture (water).

In another preferred embodiment, the fluid run through the second microchannel is a hygroscopic liquid. A hygroscopic liquid absorbs water from its surroundings. Preferably, a hygroscopic liquid is one which absorbs water such that the water content of the liquid increases at least by 4% by weight of the liquid after 60 minutes in an environment of 50% humidity at a temperature of 22° C. Examples of hygroscopic fluids are polyol esters, polyalkylene glycols and polyalkene glycols, ethanolamines or alkaline metal or earth metal salt (e.g. sodium, calcium, lithium or magnesium chlorides) solutions such as aqueous solutions.

The fluid is preferably run through the second microchannel at the same time as plasma is run through the first microchannel.

In a preferred embodiment, the fluid is run through the second microchannel in a direction opposite to that of the flow of plasma through the first microchannel.

As mentioned above, the first and third microchannels are in fluid communication with each other. Thus, flow rate at the third microchannel is determined by the flow rate at the first microchannel.

In a preferred embodiment, the fluid run through the fourth microchannel is water or low-salt phosphate-buffered saline (PBS). Preferably, it is ultrapure water of Type 1 as defined according to ISO 3696:1987, such as Millipore Corporation MiliQ water. Low-salt PBS as used herein refers to PBS with a disodium hydrogen phosphate concentration lower than 10 mmol/L, a sodium chloride concentration lower than 137 mmol/L, a potassium chloride concentration lower than 2.7 mmol/L, and a potassium dihydrogen phosphate concentration lower than 1.8 mmol/L.

Preferably, the fluid is run through the fourth microchannel at a rate of 0.001 mL/min or over, preferably 0.05 mL/min or over, more preferably 0.16 mL/min or over.

The fluid is preferably run through the fourth microchannel at the same time as plasma is run through the third microchannel.

In a preferred embodiment, the fluid is run through the fourth microchannel in a direction opposite to that of the flow of plasma through the third microchannel.

In a preferred embodiment, the method of the invention comprises an initial step of obtaining the plasma which is to be subjected to the device of the invention. This can be achieved by centrifugation of whole blood. Methods of centrifugation employed for this purpose are well known in the art. Preferably, the method of centrifugation is one which allows concentrating 90% or more of the platelets, preferably 95% or more of the platelets, more preferably 99% of the platelets in whole blood at the bottom end of the plasma centrifugation fraction (as presented in a centrifugation container after centrifugation; see FIG. 3), the bottom end of the plasma being the lower 30%, 20% 10% or 5% lower volume fraction of the plasma. In a particular embodiment, whole blood is centrifuged at about 1,095 g for about 8 minutes.

The whole plasma fraction obtained by centrifugation (as opposed to only the platelet rich fraction of the whole plasma fraction obtained by centrifugation) is preferably subjected to the device of the invention. In particular embodiments, at least 95%, at least 80%, or at least 50% of the whole plasma fraction obtained by centrifugation is subjected to the device of the invention.

Similarly, the method of the invention can comprise an initial step of running at least one hydrating composition, such as water or ethanol or a combination thereof or PBS, through at least one microchannel of the device, and preferably through all microchannels of the device. This allows conditioning and sterilizing the microchannels as well as hydrating the permeable membranes.

Similarly, the method of the invention can comprise an initial step of sterilizing at least one microchannel of the device. Methods of microchannel sterilization comprise steam autoclaving, chemical sterilization (sodium hydroxide, hydrogen peroxide or ethylene oxide), UV or gamma radiation, or combinations thereof.

PRP of the Invention and Uses Thereof

In another aspect, the present invention relates to a plasma obtained by the method of the present invention.

Platelets function as exocytotic cells, secreting a plethora of effector molecules at sites of vascular injury. Platelets contain a number of distinguishable storage granules including alpha granules, dense granules and lysosomes. On activation platelets release a variety of proteins, largely from storage granules but also as the result of apparent cell lysis. These act in an autocrine or paracrine fashion to modulate cell signaling. Alpha granules contain mainly polypeptides such as fibrinogen, von Willebrand factor, growth factors and protease inhibitors that supplement thrombin generation at the site of injury. Dense granules contain small molecules, particularly adenosine diphosphate (ADP), adenosine triphosphate (ATP), serotonin and calcium, all recruit platelets to the site of injury.

As mentioned above, the plasma obtained by the method of the present invention, which can also be labelled a PRP, possesses both concentrated levels of platelets (and therefore platelet growth factors) and of non-platelet biomolecules, especially of non-platelet growth factors.

The increased concentration in platelets improves the healing properties of the plasma with respect to plasmas wherein platelets are not concentrated, such as plasma directly isolated from whole blood. This is well known in the art.

The present inventors have now surprisingly found that by also concentrating non-platelet biomolecules, especially growth factors, the regenerative potential of the plasma is boosted.

Thus, in yet another aspect, the present invention relates to a plasma obtained by the method of the present invention (hereinafter "plasma of the invention") for use in regenerative medicine. The use in regenerative medicine more particularly refers to the treatment of injured tissue in a subject.

The present invention likewise refers to a method of treatment of injured tissue in a subject of need thereof, comprising administering to the subject plasma of the invention.

The present invention likewise refers to the use of plasma of the present invention in the preparation of a medicament for the treatment of injured tissue.

As used herein, "treating", "treatment" and the like includes abrogating, inhibiting, slowing or reversing the progression of a condition.

As used herein, the term "injured" is used in its ordinary sense to refer to any tissue damage including a wound, trauma or lesion or any tissue degeneration.

In a preferred embodiment, the injured tissue is bone.

In a preferred embodiment, the injured tissue is soft tissue.

In a more particular embodiment, the injured tissue is selected from the group consisting of connective tissue, cardiac muscle, skeletal muscle, brain tissue, corneal tissue, nerve tissue, and vascular tissue.

In another particular embodiment, the plasma of the present invention is employed in dentistry, in particular after oral surgery.

Examples of specific disease states that may be treated with the plasma of the present invention are chronic tendinitis, plantar fasciitis, osteoarthritis, or androgenic alopecia.

In particular embodiments, the plasma which is subjected to the method of the present invention and is then administered to the subject is autologous or allogenic. More preferably, it is autologous.

In another aspect, the invention relates to the cosmetic use of a plasma obtained by the method of the present invention. Particular cosmetic uses are treating skin wrinkles, striae, or dark circles under the eyes.

The plasma of the invention may be delivered at any suitable dose. In some embodiments, the dose may be between 1 mL and 20 mL. The dose is usually determined according to the specific medical procedure followed, the condition treated, and the patient profile.

The plasma of the invention may be delivered by the oral and parenteral routes, such as intravenous (iv), intraperitoneal (ip), subcutaneous (sc), intramuscular (im), rectal, topical, ophthalmic, nasal, and transdermal. The plasma of the invention may be delivered to a subject in need thereof by injection using a syringe or catheter. The plasma of the invention may also be delivered via a dermal patch, a spray device or in combination with an ointment, or bone graft. It may further be used as a coating on suture, stents, screws, plates, or some other implantable medical device. Plasma of the invention formulated as gels or other viscous fluids may be difficult to deliver via a needle or syringe. Thus, in variations where the use of a needle or syringe is desirable, it may be desirable to add a gelling and/or hardening agent to the plasma of the invention in situ.

The site of delivery of the PRP composition is typically at or near the site of tissue damage. The site of tissue damage is determined by well-established methods including imaging studies and patient feedback or a combination thereof. In some examples, the plasma of the invention may be delivered to damaged connective tissue in or around affected joints.

The invention is described below by means of the following examples which must be considered as merely illustrative and in no case limiting to the scope of the present invention.

EXAMPLES

Example 1: Microfluidic Device Fabrication

Two different microfluidic platforms were designed and constructed, one for evaporating and another for dialyzing plasma samples. Layers were fabricated with poly(methyl methacrylate) (PMMA), each of 2 mm thickness, where a long microchannel was drilled on its surface using a computer numerical control (CNC) micromilling machine (Protomat C100/HF, LPKF Laser & Electronics, Garbsen, Germany). Both layers were joined together, such that both microchannels were face-off but separated by a regenerated cellulose membrane. In case of the evaporation platform, a 10-20 kDa membrane (25-30 Å-pore, cellulose hydrate, Nadir®-dialysis tubing) was used, while a 1 kDa membrane (Spectra/Por® 7, Spectrum Labs) was employed for the dialysis platform. Sealing of the system was done by a homemade aluminum holder. Inlets and outlets were placed de-aligned to avoid any possible membrane break due to the different flows. In the case of the evaporation platform, the microchannel was of 1000 μm width, 150 μm depth, and 230 mm length. The dimensions for the dialysis platform microchannel were the same except for the length, which was of 115 mm. Device inlets and outlets were connected to 0.8 mm-diameter polytetrafluoroethylene (PTFE) tube, ensuring the sealing of the device through o-rings.

Example 2: Preparation of Plasma of the Invention

The device of Example 1 was employed for preparing plasma of the present invention.

The evaporation platform was placed onto a hot plate for heating the plasma sample to 37° C. (corresponding to 45° C. for the hot plate). The temperature of the plasma sample was checked at the outlet of the microfluidic device. The upper layer was used for flowing 12 mL of plasma sample, while a nitrogen stream at 0.01-1.0 bar was supplied in the lower layer. Thus, the inlet from the lower layer was connected to a nitrogen bottle, while the outlet tube ended in a waste container. The inlet from the upper layer was connected to a syringe for pumping of plasma sample, and the outlet tube was coupled to the dialysis platform inlet.

The upper layer of the dialysis platform was also used to flow the plasma sample, while Milli-Q water was pumped in the lower layer. Thus, the inlet from the lower layer was connected to a syringe filled with Milli-Q water, and the outlet tube finished in a waste container.

Standard syringe pumps (NE-1000, New Era Pump Systems, Inc.) were used to push the plasma samples and Milli-Q water at a flow rate of 0.04 mL/min and 0.16 mL/min, respectively. In both platforms, flows from the upper and lower layers were operated in opposite direction. Plasma was recirculated thrice through the device.

Prior to use, both platforms were greatly rinsed with Milli-Q water, 70% ethanol, Milli-Q water again, and finally PBS 1×.

Example 3: Blood Plasma Samples for Analysis

Blood samples were obtained from healthy volunteers between 18 to 65 years old. Once blood was drawn from the patient, the sample was processed in three different ways.

PRP-A

One aliquot was centrifuged at 1,095 g for 8 min and the whole volume of plasma was collected to perform the assays. This 1× fraction (PRP-A) contains an equal concentration of plasmatic and platelet growth factors (GFs), and whose levels are the same as in blood.

PRP-B

A second aliquot was centrifuged at 1,095 g for 8 min to collect the 1× plasma fraction, as for PRP-A, but was then treated with the microfluidic device of the invention (see Example 2 above), for the concentration of both platelets and non-platelet biomolecules.

PRP-C

A third aliquot was treated with a commercial kit (PRGF®-Endoret®, BTI Biotechnology Institute), which allows obtaining plasma enriched in platelets by centrifugation.

Example 4: Comparative Studies

Diverse analyses and assays were performed on samples PRP-A, PRP-B and PRP-C. Firstly, platelet concentration was quantified; secondly, the integrity of platelets was evaluated by flow cytometry; thirdly, the concentration of two different growth factors was determined using ELISA assays; and fourthly, the bioactivity of the plasma preparations was tested.

Platelet Quantification

Concentration of platelets in plasma was quantified using a blood automated analyzer (ADVIA® 120 System, Siemens) in an external analysis laboratory (General Lab, Labco Diagnosis). PRP-A, PRP-B and PRP-C samples were analyzed without any further treatment or dilution.

Figure 5:
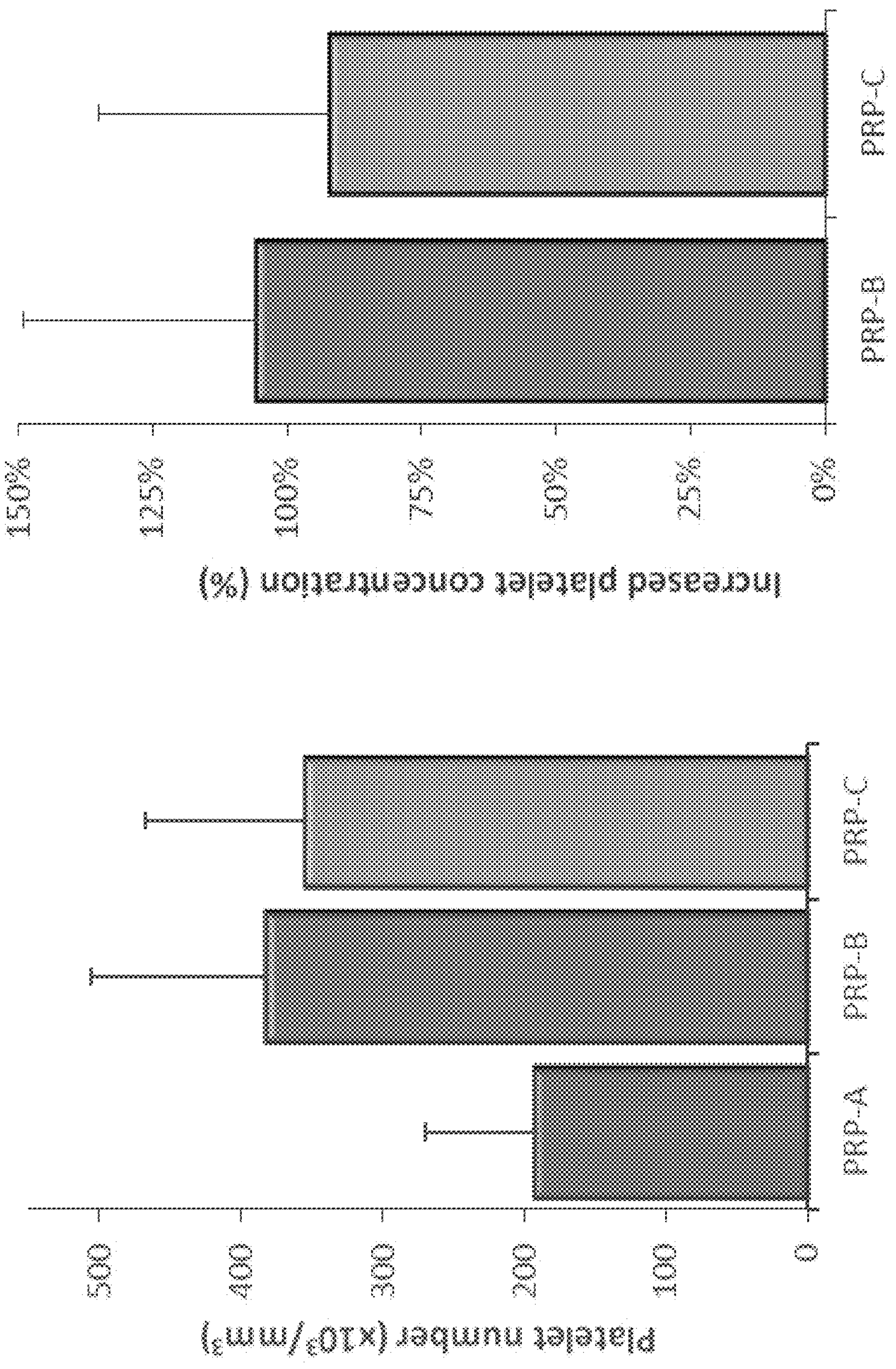
FIG. 5. Left: Platelet quantification of PRP samples tested (n=9). Right: Comparison of the increased concentration of platelets for PRP-B and PRP-C with respect to levels found in PRP-A (n=9).

Nine different samples were analyzed and, as can be observed in FIG. 5, samples treated with the proposed microfluidic device (PRP-B) showed an increment in the concentration of platelets when compared with the basal sample (PRP-A). Platelets were concentrated around 100% for most of the samples tested. Furthermore, the increase in platelet concentration for plasma samples prepared according to the present invention (PRP-B) were higher than those prepared by the prior art method (PRP-C).

Platelet Integrity

Platelet integrity was evaluated to determine possible cell damages on platelet structure and physiology during the procedures to obtain the different plasma preparations.

CD62 molecule or P-selectin is a component of the granule membrane, which mediates adhesion of activated platelets with other leukocytes (e.g. neutrophils). Circulating degranulated platelets rapidly lose CD62 expression on the surface. Thus, platelets from the three different preparations were evaluated and compared between them using flow cytometry, since this technique is routinely used for the study of platelet activation and aggregation status.

Platelet integrity was studied by flow cytometry. P-selectin/CD62 adhesion molecule, involved in the interaction between activated platelets and neighboring cells, was selected as an indicator of bioactive platelets. An aliquot of 100 μL of each plasma preparation was collected and 2 μL of anti-human CD62P APC-conjugated (from Thermo Fisher Scientific) was added for 1 h at RT, to stain functional platelets. Platelets were washed for 10 min at 2,000 g and flow cytometry was carried out in a Novocyte Flow Cytometer (ACEA Biosciences, Inc.) equipped with a 640 nm laser excitation source and 675/30 nm detection filter (APC-H channel).

Figure 6:
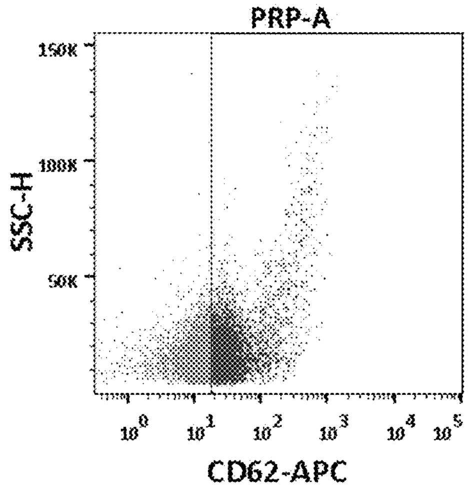
FIG. 6. Flow cytometry of platelets from PRP-A, PRP-B and PRP-C plasma preparations. CD62/p-selectin positive platelets are presented in dark gray (APC channel).
Figure 6:
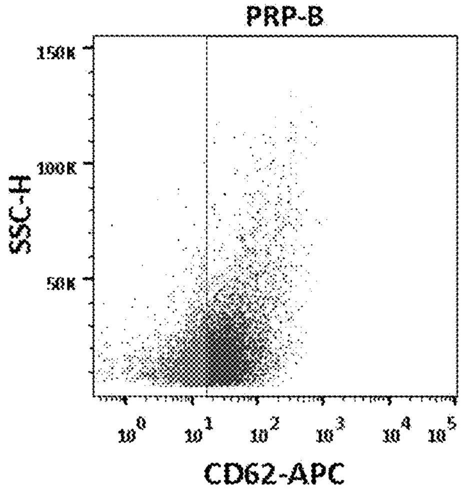
Figure 6:
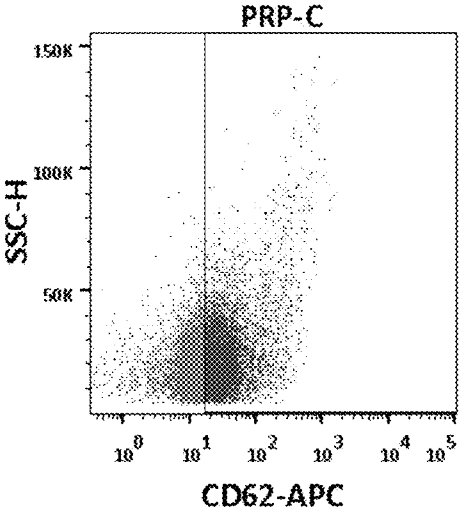

As it can be observed in FIG. 6, no significant differences appear in the cytometric analysis of platelets from each plasma preparation, detecting around 70% of activated/functional platelets (CD62 positive).

HGF and IGF-I Quantification

Hepatocyte growth factor (HGF) and insulin-like growth factor I (IGF-I) were chosen as targets of study due to their important role in cell growth, migration and differentiation in healing processes of bone or soft tissues. Human HGF is secreted as a pro-peptide, which is activated at sites of tissue damage. IGF-I directly binds with insulin receptors promoting cell growing and proliferation signaling. Levels of HGF and IGF-I have been routinely evaluated as biomarkers for different associated diseases due to their presence in plasma.

ELISA assays for each growth factor were used to determine the concentration values of PRP-A, PRP-B and PRP-C samples.

Collected PRP-A, PRP-B and PRP-C were centrifuged at 2,000 g for 15 min to pull down the platelet content. Plasma supernatants were stored at −20° C. until use. HGF and IGF-I levels were quantified with a HGF Quantikine enzyme-linked immunoabsorbed assay ELISA kit and IGF-I Quantikine ELISA kit (R&D Sytems). Samples were pretreated as recommended for IGF-I quantification, prior to assay. Plasmas were incubated for 2 h with a primary anti-HGF or anti-IGF-I antibodies followed by 1 h incubation with a secondary HRP-labeled antibody. HRP substrate was added for 30 min and absorbance was measured at 450 nm with a Multimode Plate Reader Tristar 2S (Berthold Technologies GmbH, Germany). All standards and plasmas were assayed in triplicate and growth factors concentrations were extrapolated from calibration curves.

Figure 7:
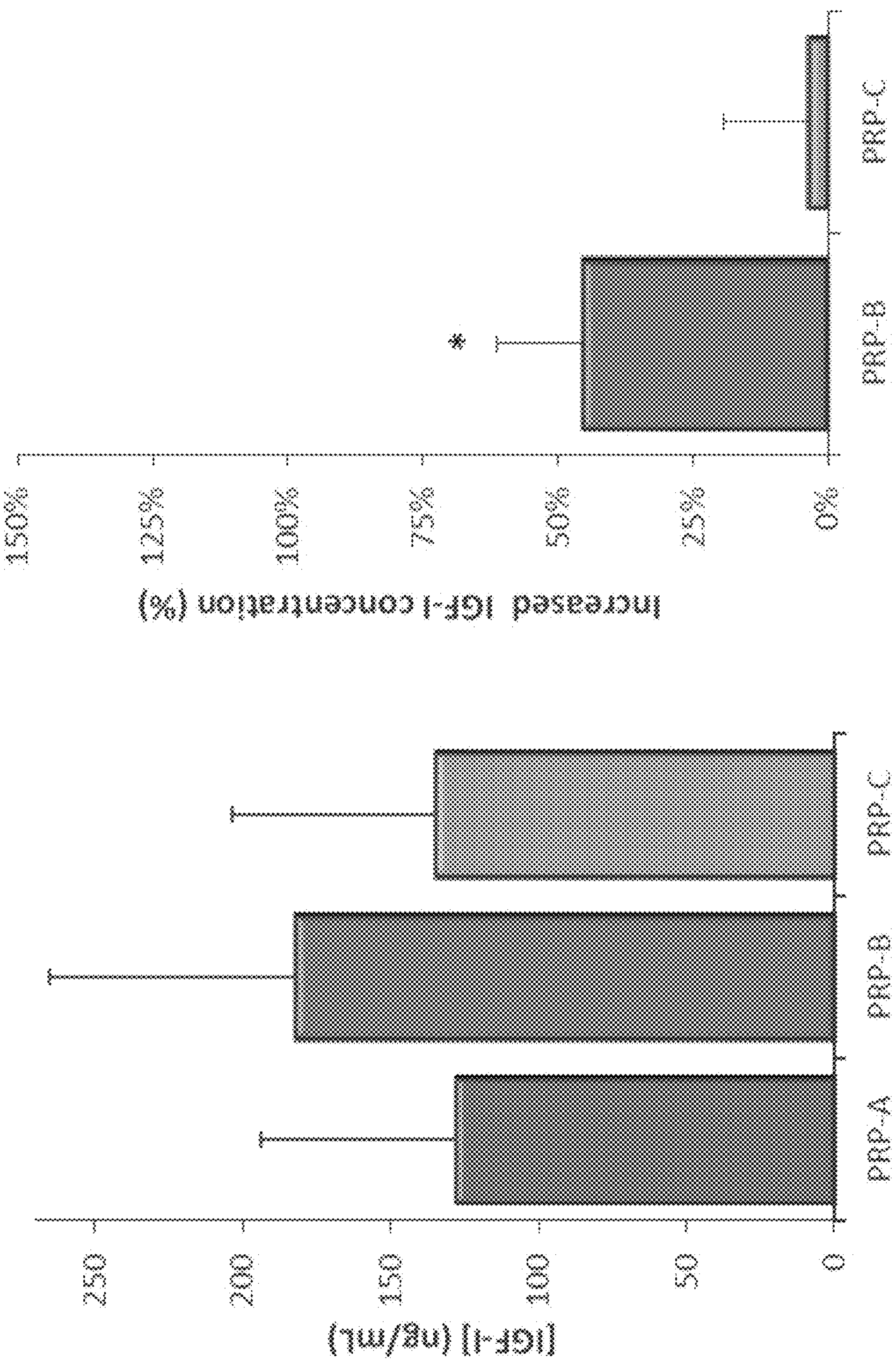
FIG. 7. Left: IGF-I levels, quantified by ELISA assay, in PRP-A, PRP-B and PRP-C (n=9). Right: Comparison of the increased concentration (%) for IGF-I in PRP-B vs PRP-C plasma (n=9). *$p<0.05$ with respect to PRP-C.

As can be observed in FIG. 7, the average basal levels of IGF-I (PRP-A) for nine different healthy donors were circa 127 ng/mL (ranging values between 35-245 ng/mL). Samples treated using the Endoret® technology (PRP-C) showed equivalent protein concentration, since an average value of 134 ng/mL IGF-I concentration was obtained (ranging values between 45-250 ng/mL). On the contrary, a considerable increment of the protein concentration was observed for PRP-B samples, attaining an average value of 181 ng/mL (ranging values between 65-350 ng/mL). Indeed, this increase in the concentration of the protein involves up to 50% when comparing PRP-B with PRP-C ($p<0.05$) (FIG. 7).

Figure 8:
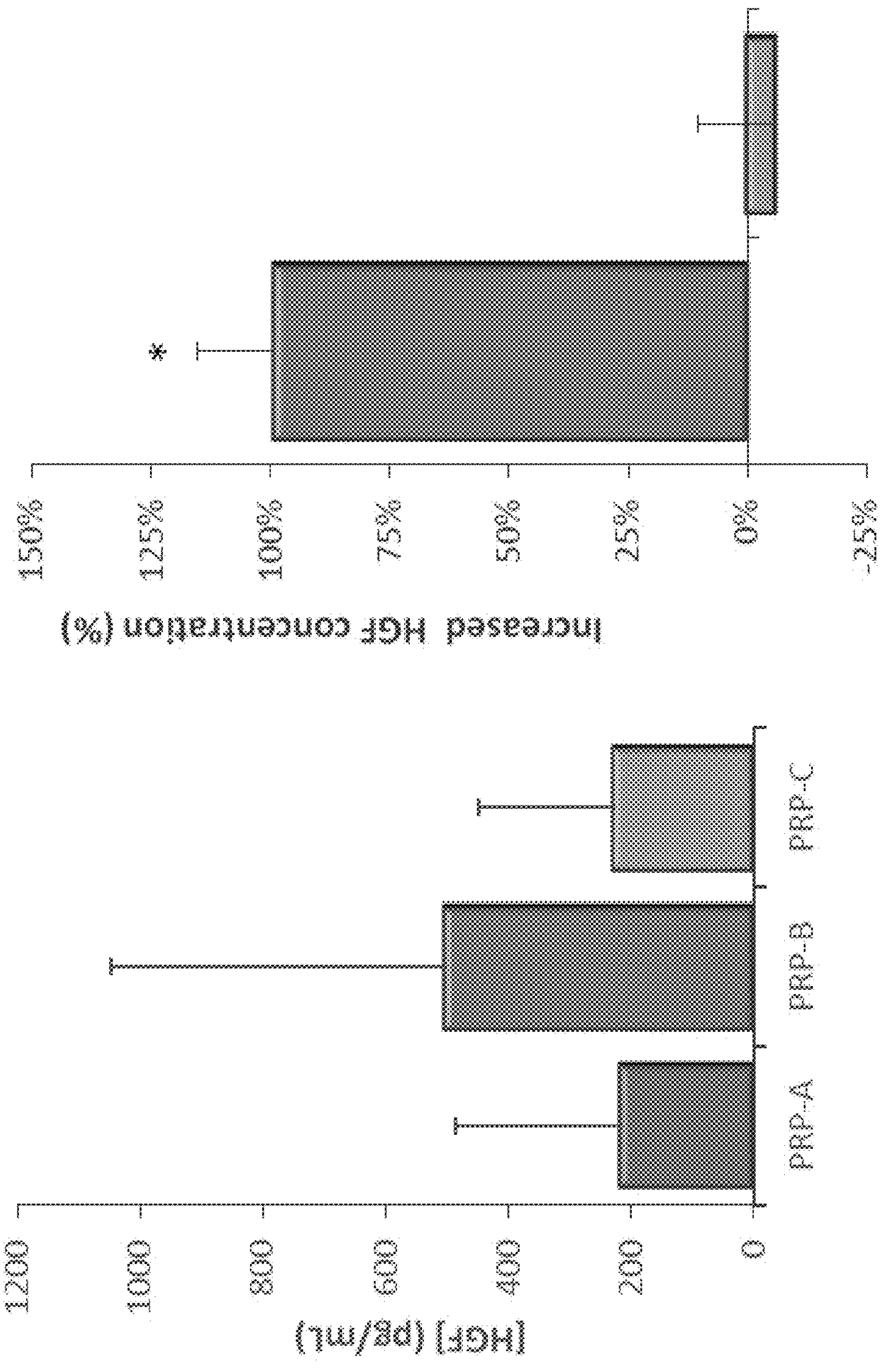
FIG. 8. Left: HGF levels, quantified by ELISA assay, in PRP-A, PRP-B and PRP-C (n=9). Right: Comparison of the increased concentration (%) for HGF in PRP-B vs PRP-C plasma (n=9). *$p<0.05$ with respect to PRP-C.

A similar trend was observed for HGF samples, where the average normal levels in plasma found were of 215 pg/mL (PRP-A) as it can be seen in FIG. 8 (values between 40-800 pg/mL). Again, samples treated using the commercial kit (PRP-C) showed equivalent concentration of the protein for most of cases, 227 pg/mL. On the contrary, the use of the proposed microfluidic device provided higher concentration of the growth factor for all samples, since an average value of 503 pg/mL was attained (values between 700-1750 pg/mL).

Bioactivity Tests

Biological activity of each PRP was studied by cell proliferation assays.

Normal human dermal fibroblasts (NHDF) (purchased from American Type Culture Collection, Manassas, USA) were maintained in fibroblast basal media (FBM) supplemented with 2% fetal bovine serum, 0.1% insulin, 0.1% human recombinant fibroblast growth factor (FGF-B) and 0.1% gentamicin (GA)-1000 (Lonza) and endothelial growth media (EGM-2) supplemented with 2% fetal bovine serum, 0.04% hydrocortisone, 0.4% human FGF-B, 0.1% vascular endothelial growth factor (VEGF), 0.1% IGF-I, 0.1% ascorbic acid, 0.1% human epidermal growth factor (EGF), 0.1% GA-1000 and 0.1% heparin, respectively, at 37° C., 5% $CO_2$ in a humidified atmosphere.

Firstly, PRP-A, PRP-B and PRP-C plasmas were activated adding 20 μL of $CaCl_2$) per 1 mL of volume, for 2-4 h at 37° C. After fibrin coagula formation, the clot was removed and supernatants were stored at −20° C. until use. 3,000 NHDFs/well were seeded onto 96 microtiter well-plates and left for attachment overnight. Following day, cells were treated with basal media without FBS, as negative control; basal media with 2% PRP-A, 2%

PRP-B and 2% PRP-C supernatants. Complete growth media was used as positive control treatment. Cells were left in treatment for 0-9 days and metabolic activity was evaluated daily adding media with 10% Cell Counting Kit-8 (Sigma Aldrich). After 4 h, supernatants were transferred to a new plate and absorbance was measured at 450 nm with a Multimode Plate Reader Tristar 2S (Berthold). All samples were assayed in triplicate. Additionally, cells were inspected by microscopy techniques. NHDF cells were fixed with paraformaldehyde 4% in PBS for 20 min and washed three times with PBS 1×. Then, 50 pg/mL of wheat germ agglutinin AlexaFluor555 conjugate were incubated for 1 h to stain cell walls, they were washed and 100 nM DAPI were added for nuclei staining. Samples were evaluated under a fluorescent microscope equipped with 540/25 nm excitation source and 605/55 nm emission filter.

Figure 9:
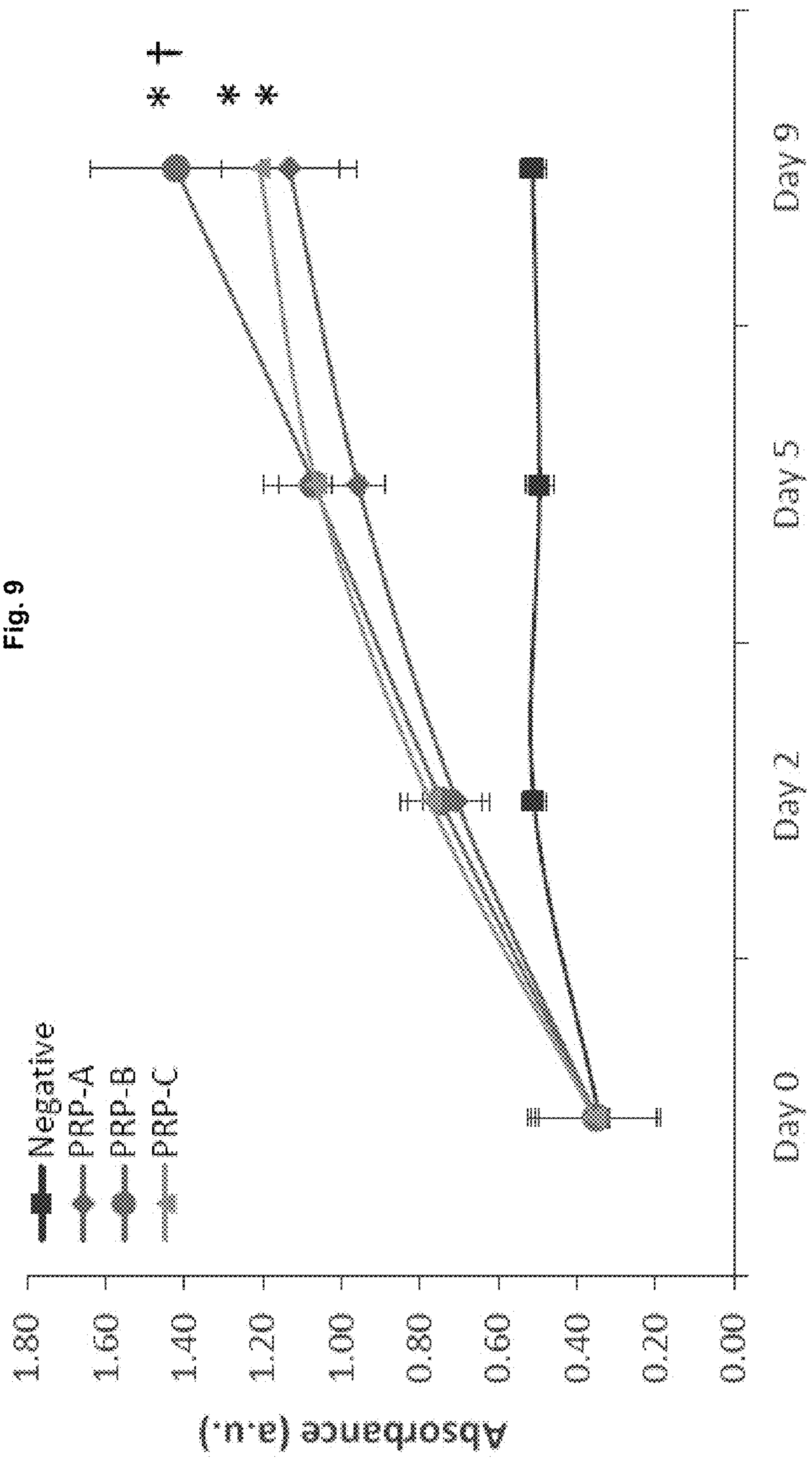
FIG. 9. Absorbance values at 450 nm for CCK-8 proliferation assay (n=5). Metabolic activity is measured as index of cell number. *$p<0.05$ with respect to negative control, †$p<0.05$ with respect to Day 5.
Figure 10:
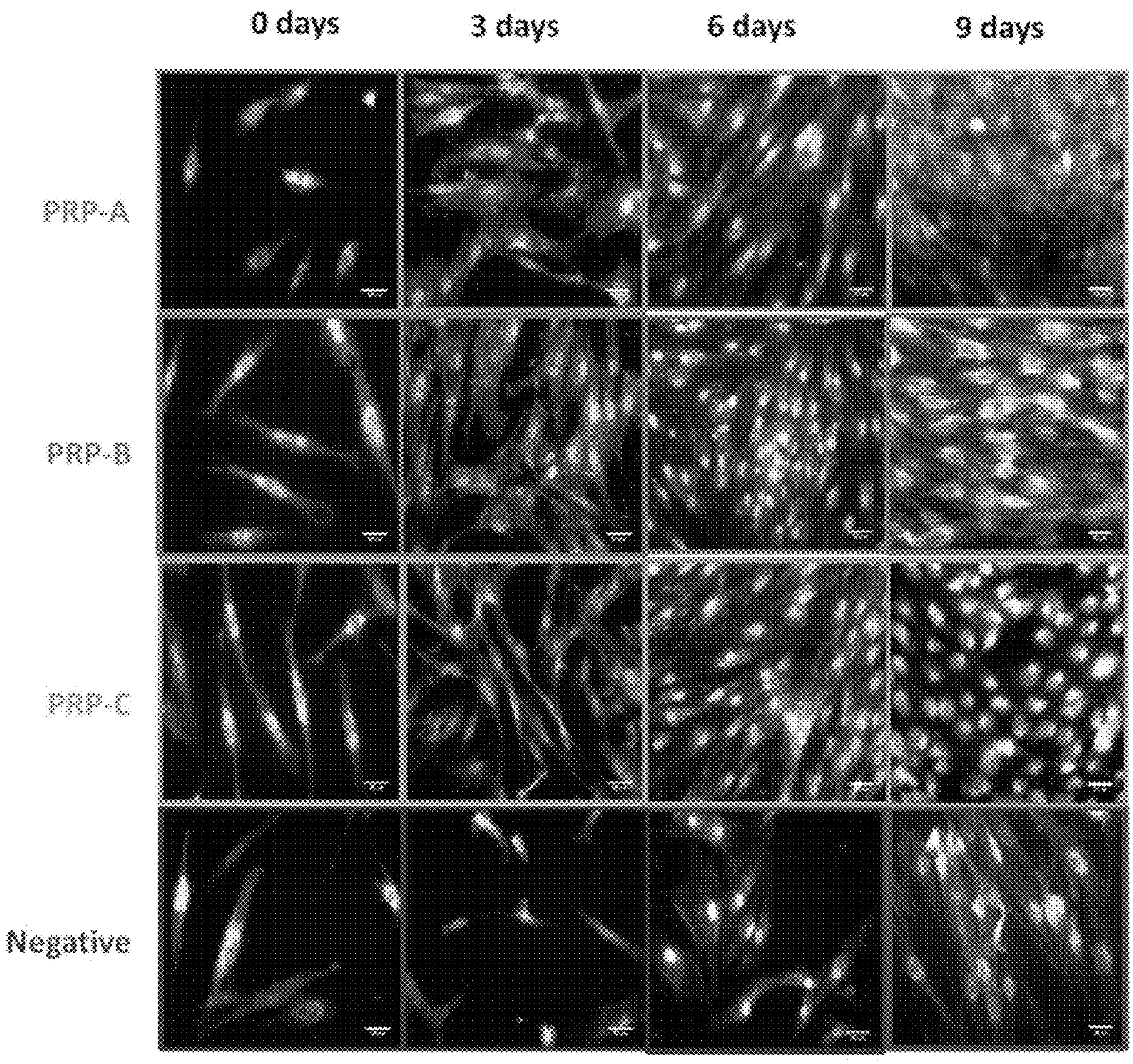
FIG. 10. Fluorescence images from the proliferation assay for one of the studied patients.

As can be observed in FIG. 9, cells exposed to basal media supplemented with 2% PRP-A show a higher proliferation than when exposed to basal media only (negative control), as expected. A similar trend of cell growth is observed for the treated with PRP-C and PRP-B preparations ($p<0.05$). Major content on platelets, and consequently major platelet-derived growth factors, can be an explanation of this increase. Notably, the PRP-B treatment increased bioactivity from day 5 to day 9, contrary to PRP-A and PRP-C preparations the activity of which plateaus after day 5 ($p<0.05$).

The invention claimed is:

1. Microfluidic device for preparation of platelet rich plasma (PRP) enriched in non-platelet biomolecules, comprising:

a first platform adapted for evaporating plasma comprising:

a first layer comprising a first microchannel formed on a first surface of said first layer;

a second layer comprising a second microchannel formed on a first surface of said second layer; and a first permeable membrane with a molecular-weight cutoff (MWCO) between 10 Dalton and 20 kDalton, placed between the first and second layer;

wherein the first surfaces of the first and second layers face each other and are in contact with the first permeable membrane;

wherein the first permeable membrane covers the first and second microchannels, such that plasma can flow through the first microchannel and fluid can flow through the second microchannel;

wherein the first and second microchannels are spatially arranged with respect to each other such that molecules that evaporate from the first microchannel and cross the first permeable membrane are received in the second microchannel;

wherein the first microchannel comprises a first inlet for inputting plasma and a first outlet for outputting plasma, and the second microchannel comprises a second inlet for inputting fluid and a second outlet for outputting fluid;

a second platform adapted for dialyzing plasma comprising:

a third layer comprising a third microchannel formed on a first surface of said third layer;

a fourth layer comprising a fourth microchannel formed on a first surface of said fourth layer; and a second permeable membrane with a molecular-weight cutoff (MWCO) between 100 Dalton and 1 kDalton, placed between the third and fourth layer;

wherein the first surfaces of the third and fourth layers face each other and are in contact with the second permeable membrane;

wherein the second permeable membrane covers the third and fourth microchannels, such that plasma can flow through the third microchannel and fluid can flow through the fourth microchannel;

wherein the third and fourth microchannels are spatially arranged with respect to each other such that molecules that diffuse from the third microchannel and across the second permeable membrane are received in the fourth microchannel;

wherein the third microchannel comprises a third inlet for inputting plasma and a third outlet for outputting plasma, and the fourth microchannel comprises a fourth inlet for inputting fluid and a fourth outlet for outputting fluid; and wherein the first outlet is in fluid communication with the third inlet, or the third outlet is in fluid communication with the first inlet.

2. Device according to claim 1, wherein the first, second, third and/or fourth layer is made of a polymeric material.

3. Device according to claim 1, wherein the first and/or second permeable membrane is a cellulose, cellulose ester, nitrocellulose, polysulfone, polyamide, polyimide, polyethylene, polypropylene, polytetrafluoroethylene, polyvinylidene fluoride, or polyvinylchloride membrane.

4. Device according to claim 3, wherein the first and/or second permeable membrane is a regenerated cellulose membrane.

5. Device according to claim 2, wherein the polymeric material is selected from the group consisting of polymethylmethacrylate, polycarbonate, polyethylene, polypropylene, a cyclic olefin polymer and a cyclic olefin copolymer.

6. Method for the preparation of platelet-rich plasma (PRP) enriched in non-platelet biomolecules, comprising the following steps:

a) providing a device as defined in claim 1;

b) providing a plasma sample;

c) inputting the plasma sample into the first microchannel; and flowing the plasma sample through the first microchannel to evaporate the plasma sample;

d) flowing the plasma sample flowed through the first microchannel through the third microchannel to dialyse the plasma sample; and e) outputting the plasma sample from the third microchannel, or alternatively c) inputting the plasma sample into the third microchannel; and flowing the plasma sample through the third microchannel to dialyse the plasma sample;

d) flowing the plasma sample flowed through the third microchannel through the first microchannel to evaporate the plasma sample; and e) outputting the plasma sample from the first microchannel.

7. Method according to claim 6, wherein the method is carried out with the device oriented in space such that the second and fourth layers lie respectively beneath the first and third layers.

8. Method according to claim 6, wherein the evaporation of the plasma sample is enhanced by heating the plasma sample prior to inputting it into the first microchannel or heating the plasma sample as it is run through the first microchannel.

9. Method according to claim 6, wherein the evaporation of the plasma sample is enhanced by flowing a fluid, an inert gas, through the second microchannel, at the same time as the plasma sample is flowed through the first microchannel.

10. Method according to claim 6, wherein the evaporation of the plasma sample and dialysis are enhanced by recirculating plasma outputted from the device back into the device at least once.

11. Method according to claim 6, wherein the evaporation of the plasma sample is enhanced by flowing a fluid, preferably water, through the fourth microchannel, at the same time as the plasma sample is flowed through the third microchannel.

12. Method according to claim 9, wherein the flow of plasma and the flow of fluid run in opposite directions.

* * * * *